(12) United States Patent
Ericson et al.

(10) Patent No.: US 9,833,538 B2
(45) Date of Patent: *Dec. 5, 2017

(54) ADHESIVE COMPOSITIONS AND RELATED METHODS

(71) Applicant: Xcede Technologies, Inc., Rochester, MN (US)

(72) Inventors: Daniel Grant Ericson, Rochester, MN (US); Kyle Robert Brandy, New Hope, MN (US)

(73) Assignee: Xcede Technologies, Inc., Rochester, MN (US)

( * ) Notice: Subject to any disclaimer, the term of this patent is extended or adjusted under 35 U.S.C. 154(b) by 16 days.

This patent is subject to a terminal disclaimer.

(21) Appl. No.: 14/983,396

(22) Filed: Dec. 29, 2015

(65) Prior Publication Data

US 2017/0035930 A1 Feb. 9, 2017

Related U.S. Application Data

(63) Continuation-in-part of application No. 14/821,625, filed on Aug. 7, 2015, now Pat. No. 9,540,548.

(60) Provisional application No. 62/202,707, filed on Aug. 7, 2015.

(51) Int. Cl.
*A61L 26/00* (2006.01)
*C09J 133/02* (2006.01)
*A61L 15/58* (2006.01)
*A61L 15/40* (2006.01)

(52) U.S. Cl.
CPC .......... *A61L 26/0014* (2013.01); *A61L 15/40* (2013.01); *A61L 15/58* (2013.01); *C09J 133/02* (2013.01)

(58) Field of Classification Search
CPC ...... A61L 26/0014; A61L 15/40; A61L 15/58; C08L 31/02; C09J 133/02
See application file for complete search history.

(56) References Cited

U.S. PATENT DOCUMENTS

| | | |
|---|---|---|
| 2,492,458 A | 12/1949 | Bering, Jr. |
| 2,533,004 A | 12/1950 | Ferry et al. |
| 2,576,006 A | 11/1951 | Ferry et al. |
| 3,523,807 A | 8/1970 | Gerendas |
| 3,558,418 A | 1/1971 | Porter et al. |
| 4,181,557 A | 1/1980 | Buccigross et al. |
| 4,347,841 A | 9/1982 | Benyó et al. |
| 4,359,047 A | 11/1982 | Potaczek |
| 4,699,146 A | 10/1987 | Sieverding |
| 4,732,755 A | 3/1988 | Grana |
| 4,790,819 A | 12/1988 | Li et al. |
| 4,909,251 A | 3/1990 | Seelich |
| 5,013,769 A | 5/1991 | Murray et al. |
| 5,209,776 A | 5/1993 | Bass et al. |
| 5,219,328 A | 6/1993 | Morse et al. |
| 5,225,473 A | 7/1993 | Duan |
| 5,290,552 A | 3/1994 | Sierra et al. |
| 5,292,362 A | 3/1994 | Bass et al. |
| 5,318,524 A | 6/1994 | Morse et al. |
| 5,407,671 A | 4/1995 | Heimburger et al. |
| 5,437,292 A | 8/1995 | Kipshidze et al. |
| 5,464,471 A | 11/1995 | Whalen et al. |
| 5,480,649 A | 1/1996 | Akazawa et al. |
| 5,549,904 A | 8/1996 | Juergensen et al. |
| 5,571,181 A | 11/1996 | Li |
| 5,585,007 A | 12/1996 | Antanavich et al. |
| 5,630,842 A | 5/1997 | Brodniewicz |
| 5,631,011 A | 5/1997 | Wadström |
| 5,643,192 A | 7/1997 | Hirsh et al. |
| 5,649,959 A | 7/1997 | Hannam et al. |
| 5,686,180 A | 11/1997 | Rivlin et al. |
| 5,702,715 A | 12/1997 | Nikolaychik et al. |
| 5,716,645 A | 2/1998 | Tse et al. |
| 5,736,132 A | 4/1998 | Juergensen et al. |
| 5,739,288 A | 4/1998 | Edwardson et al. |
| 5,750,657 A | 5/1998 | Edwardson et al. |
| 5,763,410 A | 6/1998 | Edwardson et al. |
| 5,763,411 A | 6/1998 | Edwardson et al. |
| 5,770,194 A | 6/1998 | Edwardson et al. |
| 5,773,418 A | 6/1998 | Edwardson et al. |
| 5,788,662 A | 8/1998 | Antanavich et al. |
| 5,795,571 A | 8/1998 | Cederholm-Williams et al. |
| 5,795,780 A | 8/1998 | Cederholm-Williams et al. |
| 5,804,428 A | 9/1998 | Edwardson et al. |
| 5,844,087 A | 12/1998 | Zimmerman et al. |
| 5,883,078 A | 3/1999 | Seelich et al. |
| 5,962,026 A | 10/1999 | Edwardson et al. |
| 5,962,420 A | 10/1999 | Edwardson et al. |
| 5,977,313 A | 11/1999 | Heath et al. |

(Continued)

FOREIGN PATENT DOCUMENTS

AU 2005203703 A1 9/2005
JP H10-510183 A 10/1998

(Continued)

OTHER PUBLICATIONS

Office Communication dated Mar. 4, 2014 for Application No. 13/644,889.
Notice of Allowance dated Jan. 28, 2015 for U.S. Appl. No. 13/644,889.
Office Communication dated Feb. 25, 2014 for U.S. Appl. No. 13/644,907.
Office Communication dated Sep. 11, 2014 for U.S. Appl. No. 13/644,907.
Invitation to Pay Additional Fees for PCT/US2013/024322 dated May 29, 2013.

(Continued)

*Primary Examiner* — Robert Jones, Jr.
(74) *Attorney, Agent, or Firm* — Wolf, Greenfield & Sacks, P.C.

(57) ABSTRACT

Adhesive compositions and patches, and associated systems, kits, and methods, are generally described. Certain of the adhesive compositions and patches can be used to treat tissues (e.g., in hemostatic or other tissue treatment applications), according to certain embodiments.

32 Claims, 7 Drawing Sheets

(56) References Cited

U.S. PATENT DOCUMENTS

| | | |
|---|---|---|
| 5,985,315 A | 11/1999 | Patat et al. |
| 6,007,811 A | 12/1999 | Sawyer et al. |
| 6,015,474 A | 1/2000 | Stedronsky |
| 6,019,993 A | 2/2000 | Bal |
| 6,043,407 A | 3/2000 | Lodhi et al. |
| 6,048,966 A | 4/2000 | Edwardson et al. |
| 6,063,061 A | 5/2000 | Wallace et al. |
| 6,063,297 A | 5/2000 | Antanavich et al. |
| 6,074,663 A | 6/2000 | Delmotte et al. |
| 6,077,507 A | 6/2000 | Edwardson et al. |
| 6,162,241 A | 12/2000 | Coury et al. |
| 6,200,587 B1 | 3/2001 | Soe et al. |
| 6,214,338 B1 | 4/2001 | Antanavich et al. |
| 6,251,370 B1 | 6/2001 | Uchida et al. |
| 6,258,872 B1 | 7/2001 | Stedronsky |
| 6,262,236 B1 | 7/2001 | Edwardson et al. |
| 6,268,483 B1 | 7/2001 | Edwardson et al. |
| 6,342,250 B1 | 1/2002 | Masters |
| 6,368,298 B1 | 4/2002 | Beretta et al. |
| 6,395,288 B1 | 5/2002 | Woolverton |
| 6,440,427 B1 | 8/2002 | Wadström |
| 6,444,228 B1 | 9/2002 | Baugh et al. |
| 6,447,774 B1 | 9/2002 | Metzner |
| 6,465,091 B1 | 10/2002 | Ou-Yang |
| 6,492,494 B1 | 12/2002 | Cederholm-Williams |
| 6,500,427 B1 | 12/2002 | Heimburger et al. |
| 6,503,527 B1 | 1/2003 | Whitmore |
| 6,506,365 B1 | 1/2003 | Redl et al. |
| 6,528,483 B2 | 3/2003 | Beaulieu et al. |
| 6,534,693 B2 | 3/2003 | Fischell et al. |
| 6,548,729 B1 | 4/2003 | Seelich et al. |
| 6,559,119 B1 | 5/2003 | Burgess et al. |
| 6,576,685 B2 | 6/2003 | Stedronsky |
| 6,579,537 B2 | 6/2003 | Seelich et al. |
| 6,613,324 B1 | 9/2003 | Blombäck et al. |
| 6,613,325 B1 | 9/2003 | Amery et al. |
| 6,699,484 B2 | 3/2004 | Whitmore et al. |
| 6,706,780 B2 | 3/2004 | Goldberg et al. |
| 6,723,781 B1 | 4/2004 | Frate et al. |
| 6,733,774 B2 | 5/2004 | Stimmeder |
| 6,762,336 B1 | 7/2004 | MacPhee et al. |
| 6,780,411 B2 | 8/2004 | Lewis, Jr. et al. |
| 6,824,792 B2 | 11/2004 | Foreman et al. |
| 6,875,796 B2 | 4/2005 | Stedronsky |
| 6,891,077 B2 | 5/2005 | Rothwell et al. |
| 6,916,911 B1 | 7/2005 | Bar et al. |
| 6,921,387 B2 | 7/2005 | Camrud |
| 6,921,532 B1 | 7/2005 | Austin et al. |
| 6,942,880 B1 | 9/2005 | Dolecek |
| 6,979,307 B2 | 12/2005 | Beretta et al. |
| 7,045,601 B2 | 5/2006 | Metzner et al. |
| 7,052,713 B2 | 5/2006 | Stimmeder |
| RE39,192 E | 7/2006 | MacPhee et al. |
| 7,091,015 B1 | 8/2006 | Redl et al. |
| 7,091,325 B2 | 8/2006 | Redl et al. |
| RE39,298 E | 9/2006 | MacPhee et al. |
| RE39,321 E | 10/2006 | MacPhee et al. |
| 7,141,428 B2 | 11/2006 | McKerracher |
| 7,189,410 B1 | 3/2007 | Drohan et al. |
| 7,196,054 B1 | 3/2007 | Drohan et al. |
| 7,198,786 B2 | 4/2007 | Redl et al. |
| 7,208,179 B1 | 4/2007 | Drohan et al. |
| 7,211,651 B2 | 5/2007 | Pathak |
| 7,226,657 B1 | 6/2007 | Delmotte et al. |
| 7,229,633 B2 | 6/2007 | Austin et al. |
| 7,229,959 B1 | 6/2007 | Drohan et al. |
| 7,235,255 B2 | 6/2007 | Austin et al. |
| 7,241,603 B2 | 7/2007 | Seelich et al. |
| 7,276,235 B2 | 10/2007 | Metzner et al. |
| 7,285,580 B2 | 10/2007 | Stedronsky |
| 7,303,759 B2 | 12/2007 | Mershon |
| 7,326,412 B2 | 2/2008 | Redl |
| 7,399,483 B2 | 7/2008 | Stimmeder |
| 7,427,607 B2 | 9/2008 | Suzuki |
| 7,459,295 B2 | 12/2008 | Redl et al. |
| 7,494,971 B2 | 2/2009 | Eibl |
| 7,544,348 B2 | 6/2009 | Jacob et al. |
| 7,605,232 B2 | 10/2009 | Pathak |
| 7,662,409 B2 | 2/2010 | Masters |
| 7,745,106 B2 | 6/2010 | Beretta et al. |
| 7,790,192 B2 | 9/2010 | Sawhney et al. |
| 7,811,607 B2 | 10/2010 | Baugh et al. |
| 7,838,039 B2 | 11/2010 | Baugh et al. |
| 7,846,478 B2 | 12/2010 | Ameye et al. |
| 7,867,519 B2 | 1/2011 | de Maat et al. |
| 7,892,802 B2 | 2/2011 | Redl et al. |
| 7,934,603 B2 | 5/2011 | Eaton et al. |
| 7,968,682 B2 | 6/2011 | Farrell |
| 8,167,842 B2 | 5/2012 | Lapeyre |
| 8,299,316 B2 | 10/2012 | Van Holten et al. |
| 8,361,504 B2 | 1/2013 | Hen et al. |
| 8,865,150 B2 | 10/2014 | Mumper et al. |
| 8,999,376 B2 | 4/2015 | Ericson |
| 9,352,067 B2 | 5/2016 | Ericson |
| 9,540,548 B1 | 1/2017 | Ericson et al. |
| 2004/0065232 A1 | 4/2004 | Lykke |
| 2005/0003012 A1 | 1/2005 | Woller et al. |
| 2006/0204555 A1 | 9/2006 | Yang et al. |
| 2006/0235121 A1 | 10/2006 | Burch |
| 2007/0160543 A1 | 7/2007 | Moller |
| 2007/0286891 A1 | 12/2007 | Kettlewell et al. |
| 2008/0091235 A1 | 4/2008 | Sirota |
| 2009/0075891 A1 | 3/2009 | MacPhee et al. |
| 2009/0099149 A1 | 4/2009 | Liu et al. |
| 2009/0239300 A1 | 9/2009 | van Holten et al. |
| 2009/0324714 A1 | 12/2009 | Liu et al. |
| 2010/0087768 A1 | 4/2010 | Forlano et al. |
| 2010/0233246 A1 | 9/2010 | Sehl et al. |
| 2010/0254900 A1 | 10/2010 | Campbell et al. |
| 2010/0316712 A1 | 12/2010 | Nangia et al. |
| 2011/0054375 A1 | 3/2011 | Smola |
| 2011/0066182 A1 | 3/2011 | Falus |
| 2011/0071499 A1 | 3/2011 | Hakimimehr et al. |
| 2011/0152924 A1 | 6/2011 | Gensini et al. |
| 2011/0196421 A1 | 8/2011 | MacPhee et al. |
| 2012/0070485 A1 | 3/2012 | Soldani et al. |
| 2012/0165414 A1 | 6/2012 | Jaunky et al. |
| 2013/0202656 A1 | 8/2013 | Ericson |
| 2013/0202674 A1 | 8/2013 | Ericson |
| 2013/0202675 A1 | 8/2013 | Ericson |
| 2014/0222067 A1 | 8/2014 | Ericson et al. |
| 2014/0271491 A1 | 9/2014 | Gittard et al. |
| 2015/0231299 A1 | 8/2015 | Ericson |
| 2016/0296657 A1 | 10/2016 | Ericson |

FOREIGN PATENT DOCUMENTS

| | | |
|---|---|---|
| WO | WO 96/17633 A1 | 6/1996 |
| WO | WO 98/22097 A | 5/1998 |
| WO | WO 03/059390 A1 | 7/2003 |
| WO | WO 03/092756 A1 | 11/2003 |
| WO | WO 2006/042311 A2 | 4/2006 |
| WO | WO 2012/030570 A1 | 3/2012 |
| WO | WO 2013/116633 A2 | 8/2013 |
| WO | WO 2016/022928 A1 | 2/2016 |

OTHER PUBLICATIONS

International Search Report and Written Opinion for PCT/US2013/024322 dated Aug. 12, 2013.
International Search Report and Written Opinion for International Application No. PCT/US2014/014002 dated Apr. 16, 2014.
International Preliminary Report on Patentability for PCT/US2014/014002 dated Aug. 13, 2015.
Browdie et al., "Tests of experimental tissue adhesive sealants," Texas Heart Institute Journal (2007);34:313-7.
Cheng et al., A review of three stand-alone topical thrombins for surgical hemostasis. Clin Ther. Jan. 2009;31(1):32-41. doi: 10.1016/j.clinthera.Jan. 5, 2009.
Dempfle et al., "Impact of fibrinogen concentration in severely ill patients on mechanical properties of whole blood clots," Blood Coagul Fibrinolysis (2008) 19: 765-770.

(56) References Cited

OTHER PUBLICATIONS

Elvin et al., "Photochemical fabrication of a highly elastic and adhesive surgical tissue sealant," European Cells and Materials (2010) vol. 20, Suppl. 3: 71 ISSN 1473-2262.
Khutoryanskaya et al., Hydrogen-bonded complexes and blends of poly(acrylic acid) and methylcellulose: nanoparticles and mucoadhesive films for ocular delivery of riboflavin. Macromol Biosci. Feb. 2014;14(2):225-34. doi: 10.1002/mabi.Mar. 13, 2013. Epub Sep. 17, 2013.
Mohamed et al., Preparation of fluconazole buccal tablet and influence of formulation expedients on its properties. Acta Pharmaceutica Sinica. Apr. 2011;46(4):460-5.
Pal et al., Rosin an important polymer for drug delivery: A short review. International Journal of Pharmaceutical Sciences Review & Research. Jul.-Aug. 2010;3(1): 35-7. ISSN 0976-044X.
Radosevich et al., "Fibrin sealant: scientific rationale, production methods, properties, and current clinical use," Vox Sanguinis (1997) 72(3):133-143.
Satturwar et al., Biodegradation and in vivo biocompatibility of rosin: a natural film-forming polymer. AAPS PharmSciTech. Oct. 22, 2003;4(4):E55.
Sierra et al., Failure characteristics of multiple-component fibrin-based adhesives. J Biomed Mater Res. Jan. 2002;59(1):1-11.
Office Communication dated Aug. 19, 2016 for EP Application No. 13704330.3.
Office Communication dated Nov. 11, 2016 for Application No. JP 2014-555745.
Office Communication dated Mar. 9, 2016 for Application No. 14/169,393.
International Search Report and Written Opinion for Application PCT/US16/45780 dated Jan. 13, 2017.
Mihalyi, Properties of Fibrin Dissolved in Urea Solutions. Acta Chemica Scandinavica. 1950;4:344-50.
Snejdrova et al., Pharmacutically Used Plasticizers. Recent Advances in Plasticizers, Chapter 3. InTech. Ed. Dr. Mohammad Luqman. Mar. 2012. pp. 45-68.
Vieira et al., Natural-based plasticizers and biopolymer films: A review. European Polymer Journal. Mar. 2011;47(3):254-63.
U.S. Appl. No. 13/644,907, filed Oct. 4, 2012, Ericson.
U.S. Appl. No. 14/630,150, filed Feb. 24, 2015, Ericson.
U.S. Appl. No. 14/169,393, filed Jan. 31, 2014, Ericson et al.
U.S. Appl. No. 14/821,625, filed Aug. 7, 2015, Ericson et al.
PCT/US2013/024322, dated May 29, 2013, Invitation to Pay Additional Fees.
PCT/US2013/024322, dated Aug. 12, 2013, International Search Report and Written Opinion.
PCT/2014/014002, dated Apr. 16, 2014, International Search Report and Written Opinion.
PCT/US2014/014002, dated Aug. 13, 2015, International Preliminary Report on Patentability.
U.S. Appl. No. 15/502,545, filed Feb. 8, 2017, Ericson et al.
Nair et al., Compaction as a method to characterise fibrin network structure: kinetic studies and relationship to crosslinking. Thromb Res. Nov. 15, 1997;88(4):381-7.

ADHESIVE COMPOSITIONS AND RELATED METHODS

RELATED APPLICATIONS

This application is a continuation-in-part of U.S. patent application Ser. No. 14/821,625, filed Aug. 7, 2015, and entitled "Adhesive Compositions and Related Methods," which is incorporated herein by reference in its entirety for all purposes. This application also claims priority under 35 U.S.C. §119(e) to U.S. Provisional Patent Application No. 62/202,707, filed Aug. 7, 2015, and entitled "Adhesive Compositions and Related Methods."

TECHNICAL FIELD

Adhesive compositions and related methods are generally described.

BACKGROUND

Hemostatic agents and tissue sealants are routinely used to prevent excess blood loss and to reconstruct tissue during surgical repair. For example, fibrin glue is commonly used to impart topical hemostasis, provide sealant properties that are suitable in certain clinical applications, and promote tissue approximation. However, in general, commercially available tissue sealants do not perform well in wet or "bleeding" applications. Current commercially available tissue sealants and hemostatic agents are generally too slow, too cumbersome, lack optimum adhesive properties, and/or lack the tensile strength required for suturing and preventing arterial blood loss. In addition, many commercially available sealants do not have the mechanical strength to address many clinical wound closure demands.

Accordingly, improved adhesive compositions and patches are desirable.

SUMMARY

Disclosed herein are adhesive compositions and patches, including related methods. Certain of the adhesive compositions and patches can be used to treat biological tissues (e.g., in hemostatic or other tissue treatment applications), according to certain embodiments. The subject matter of the present invention involves, in some cases, interrelated products, alternative solutions to a particular problem, and/or a plurality of different uses of one or more systems and/or articles.

In one set of embodiments, methods are provided. In one embodiment, a method of forming an adhesive matrix comprises establishing a mixture comprising a non-aqueous liquid, a first polyacrylic acid crosslinked with pentaerythritol and/or allyl sucrose, and a second polyacrylic acid crosslinked with divinyl glycol on a substrate, applying a non-aqueous polar solvent to the mixture on the substrate, and allowing at least a portion of the non-aqueous liquid and the non-aqueous polar solvent to evaporate to produce the adhesive matrix. In such embodiments, the amount of water in the mixture is less than or equal to about 2 wt. %, the non-aqueous solvent is made up of at least about 90 wt. % of ethanol, and after the evaporation, the sum of the amount of the non-aqueous liquid and the non-aqueous polar solvent in the adhesive matrix is between about 0.001 wt. % and about 3 wt. %.

According to certain embodiments, a method of forming an adhesive matrix comprises spraying a mixture comprising at least one non-aqueous solvent and at least one polyacrylic acid onto a substrate to form a deposit of the mixture on the substrate, wherein at least a portion of the at least one non-aqueous solvent is evaporated from the deposit to produce the adhesive matrix, and less than about 8 wt. % of the adhesive matrix is made up of liquid.

According to some embodiments, a method of forming an adhesive matrix comprises spraying a mixture comprising at least one non-aqueous solvent and at least one polyacrylic acid onto a substrate to form a deposit of the mixture on the substrate. In some such embodiments, the mixture contains the at least one non-aqueous solvent in an amount of from about 50 wt. % to about 99.9 wt. %, and the mixture contains the at least one polyacrylic acid in an amount of from about 0.1 wt. % to about 25 wt. %. In some such embodiments, at least a portion of the at least one non-aqueous solvent is evaporated from the deposit to produce the adhesive matrix.

In one set of embodiments, tissue adhesive composites are provided. In one embodiment, a tissue adhesive composite comprises a tissue adhesive film positioned on at least a portion of a substrate, wherein the tissue adhesive film comprises a first polyacrylic acid crosslinked with pentaerythritol and/or allyl sucrose, a second polyacrylic acid crosslinked with divinyl glycol, and a liquid comprising ethanol. In such embodiments, greater than or equal to about 90 wt. % of the tissue adhesive film is made up of polyacrylic acid, and less than about 8 wt. % of the tissue adhesive film is made up of the liquid.

Other advantages and novel features of the present invention will become apparent from the following detailed description of various non-limiting embodiments of the invention when considered in conjunction with the accompanying figures. In cases where the present specification and a document incorporated by reference include conflicting and/or inconsistent disclosure, the present specification shall control.

BRIEF DESCRIPTION OF THE DRAWINGS

Non-limiting embodiments of the present invention will be described by way of example with reference to the accompanying figures, which are schematic and are not intended to be drawn to scale. In the figures, each identical or nearly identical component illustrated is typically represented by a single numeral. For purposes of clarity, not every component is labeled in every figure, nor is every component of each embodiment of the invention shown where illustration is not necessary to allow those of ordinary skill in the art to understand the invention. In the figures.

DETAILED DESCRIPTION

Figure 1A:
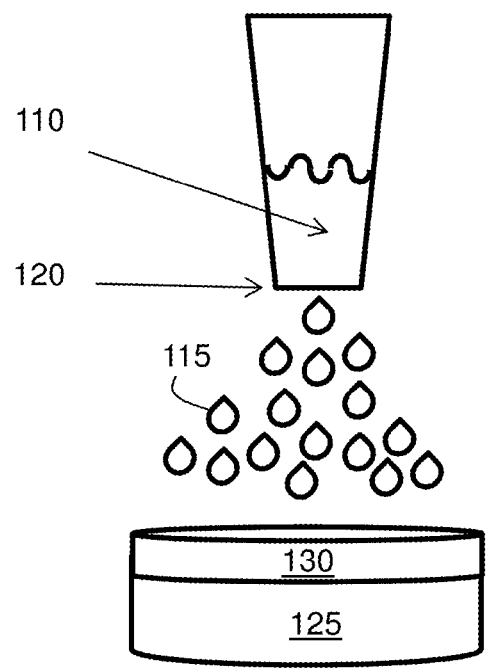
FIGS. 1A-1C are schematic illustrations showing the formation of an adhesive matrix by spraying a mixture comprising at least one non-aqueous solvent and at least one polyacrylic acid onto a substrate, according to some embodiments.

Adhesive compositions that can be used to treat biological tissues (e.g., in hemostatic or other tissue treatment applications) and related methods are provided. In some embodiments, the adhesive composition may include an adhesive matrix comprising a relatively high amount of polyacrylic acid and low amount of liquid. For instance, the adhesive composition may contain at least about 50 wt. % (e.g., at least about 75 wt. %) polyacrylic acid, but less than about 8 wt. % of liquid (e.g., 5 wt. %). In certain embodiments, the adhesive matrix comprises two or more different polyacrylic acids that can interact with one another (e.g., via hydrogen bonding) to form a strong, cohesive, and biocompatible adhesive matrix, when mixed together and applied as described herein. The resulting adhesive matrix may, according to certain although not necessarily all embodiments, have improved adherence (e.g., to biological tissue) and/or strength compared to substantially the same composition formed via a different method and/or compared to the individual polyacrylic acids alone. Methods of forming such an adhesive matrix may employ a polyacrylic acid dispersion and liquid displacement process while utilizing a relatively low amount of or no water. In another aspect, according to certain embodiments, an adhesive matrix may be formed by spraying a mixture comprising at least one non-aqueous solvent and at least one polyacrylic acid onto a substrate to form a deposit of the mixture on the substrate, wherein at least a portion of the at least one non-aqueous solvent is evaporated from the deposit to produce the adhesive matrix.

Adhesive compositions are often used in biological applications to join, seal, and/or otherwise adhere material (e.g., tissue). While numerous adhesive compositions exist, many conventional adhesive compositions face a trade-off between beneficial properties (e.g., adhesive strength, tensile strength, burst strength) and biocompatibility. That is, one or more properties (and accordingly, the utility associated with such properties) of certain conventional compositions are often limited due to the constraints imposed by the requirement for biocompatibility. There remains a need for high adhesive and mechanical strength, biocompatible adhesive compositions.

It has been discovered, according to certain although not necessarily all embodiments, that when certain polyacrylic acids (and mixtures) are subjected to processes involving dispersion in certain non-aqueous liquids, subsequent displacement of the non-aqueous liquids with certain non-aqueous solvents, and subsequent evaporation of the liquid and solvent, the resulting adhesive matrix, surprisingly, has superior adhesive and mechanical properties compared to adhesive matrices having similar or substantially the same composition formed via a different method (e.g., a single solvent method, methods in which water-based liquids are used) and compared to certain conventional biological adhesive compositions (e.g., powders, including certain polyacrylic acid powders). The resulting adhesive matrix may also have, according to certain embodiments, a relatively low liquid (e.g., residual solvent) content without the need for additional, time consuming, and/or expensive solvent removal (e.g., washing) processes.

It has also been discovered, according to certain although not necessarily all embodiments, that when mixtures comprising one or more non-aqueous solvents and one or more polyacrylic acids are sprayed onto a substrate, and at least a portion of the non-aqueous solvent(s) are evaporated from the deposit, adhesive matrices with advantageous adhesive and/or mechanical properties can be formed in certain cases.

In one set of embodiments, methods are provided. In some embodiments, a method for forming an adhesive composition comprises a dispersion step and a liquid displacement step (which may be performed subsequent to the dispersion step). The dispersion step may include establishing (e.g., distributing, applying) a mixture comprising at least one polyacrylic acid and a non-aqueous liquid on a substrate. In some cases, the polyacrylic acid(s) is relatively evenly dispersed (e.g., via dissolution or suspension) within the non-aqueous liquid, such that a relatively homogenous mixture is formed. In some such embodiments, application of the mixture to at least a portion (e.g., substantially all, the entirety) of at least one surface of the substrate may serve to relatively evenly distribute the polyacrylic acid(s) on the substrate.

As used herein, the term "non-aqueous liquid" refers to a liquid that is not water.

In some embodiments, the mixture may include a relatively low weight percentage of water. For instance, in some embodiments, the mixture contains less than or equal to about 10 wt. %, less than or equal to about 8 wt. %, less than or equal to about 6 wt. %, less than or equal to about 5 wt. %, less than or equal to about 2 wt. %, less than or equal to about 1 wt. %, less than or equal to about 0.5 wt. %, less than or equal to about 0.1 wt. %, less than or equal to about 0.05 wt. %, or less than or equal to about 0.01 wt. %. In some instances, the mixture may contain 0 wt. % water. It has been discovered that, in some embodiments, the presence of substantial amounts of water in the mixture applied to the substrate may negatively affect the adhesive and/or mechanical properties of the resulting adhesive composition.

In some embodiments, the mixture may include a relatively high weight percentage of the non-aqueous liquid(s). For instance, in some embodiments, the weight percentage of the non-aqueous liquid in the mixture may be greater than or equal to about 50%, greater than or equal to about 55 wt. %, greater than or equal to about 75 wt. %, greater than or equal to about 80 wt. %, greater than or equal to about 85 wt. %, greater than or equal to about 90 wt. %, greater than or equal to about 95 wt. %, greater than or equal to about 96 wt. %, greater than or equal to about 97 wt. %, greater than or equal to about 98 wt. %, greater than or equal to about 98.5 wt. %, greater than or equal to about 99 wt. %, or greater than or equal to about 99.5 wt. %. In some instances, the weight percentage may be less than or equal to about 100 wt. %, less than or equal to about 99.5 wt. %, less than or equal to about 99 wt. %, less than or equal to about 98.5 wt. %, less than or equal to about 98 wt. %, less than or equal to about 97 wt. %, less than or equal to about 96 wt. %, less than or equal to about 95 wt. %, less than or equal to about 90 wt. %, less than or equal to about 85 wt. %, less than or equal to about 80 wt. %, less than or equal to about 75 wt. %, less than or equal to about 70 wt. %, less than or equal to about 65 wt. %, or less than or equal to about 60 wt. %. Combinations of the above referenced ranges are also possible (e.g., greater than or equal to 50 wt. % and less than or equal to about 100 wt. %, greater than or equal to 75 wt. % and less than or equal to about 100 wt. %). According to certain embodiments, the mixture may comprise a combination of two or more non-aqueous liquids. When two or more non-aqueous liquids are present in the mixture, according to some embodiments, the total amount of all non-aqueous liquids in the mixture can be within any of the ranges outlined above.

In some embodiments, the mass ratio of the total mass of polyacrylic acid(s) to the total mass of non-aqueous liquid(s) within the mixture is from about 1:10 to about 1:1. In some embodiments, the mass ratio of the total mass of polyacrylic acid(s) to the total mass of non-aqueous liquid(s) within the mixture is greater than or equal to about 1:10, greater than or equal to about 1:9, greater than or equal to about 1:8, greater than or equal to about an 1:6, greater than or equal to about 1:5, greater than or equal to about 1:4, greater than or equal to about 1:3, greater than or equal to about 1:2, greater than or equal to about 1:1.5, or greater than or equal to about 1:1.2. In some instances, the mass ratio of the total mass of polyacrylic acid(s) to the total mass of non-aqueous liquid(s) within the mixture is less than or equal to about 1:1, less than or equal to about 1:1.2, less than or equal to about 1:1.5, less than or equal to about 1:2, less than or equal to about 1:3, less than or equal to about 1:4, less than or equal to about 1:5, less than or equal to about 1:6 less than or equal to about 1:8, or less than or equal to about 1:10. Combinations of the above-referenced ranges are also possible (e.g., greater than or equal to about 1:10 and less than or equal to about 1:1).

In general, the mixture comprising the polyacrylic acid(s) and the non-aqueous liquid(s) may be established (e.g., applied) on the substrate using a variety of suitable techniques. For instance, in some embodiments, the mixture may be applied to the substrate via casting, spin coating, dip coating, or spray coating. According to certain embodiments, the mixture of the polyacrylic acid(s) and the non-aqueous liquid(s) can be sprayed onto the substrate, for example, using any of the methods and/or parameters described below with respect to the spraying of a mixture of at least one non-aqueous solvent and at least one polyacrylic acid. In certain embodiments, the mixture may form a film on the surface of the substrate. In certain embodiments, establishing (e.g., applying) the mixture of polyacrylic acid(s) and non-aqueous liquid(s) comprises first mixing the polyacrylic acid(s) and the non-aqueous liquid(s), and subsequently applying the mixture to the substrate. In some embodiments, applying the mixture of polyacrylic acid(s) and non-aqueous liquid(s) comprises separately applying the polyacrylic acid(s) and the non-aqueous liquid(s) to the substrate, and mixing the components together to form the mixture on the substrate.

According to certain embodiments, removal of large amounts of the non-aqueous liquid prior to application of the non-aqueous polar solvent is not desirable, as such high rates of removal can lead to coagulation of the polyacrylic acid, which can result in the formation of an adhesive matrix that is not mechanically robust. However, in some cases, after application of the mixture to the substrate, a portion of the non-aqueous liquid may be removed (e.g., via evaporation) prior to addition of another liquid (e.g., the non-aqueous polar solvent described below). In some embodiments, up to about 10 wt. %, up to about 20 wt. %, up to about 30 wt. %, up to about 40 wt. %, up to about 50 wt. %, up to about 60 wt. %, up to about 70 wt. %, or more of the non-aqueous liquid may be removed prior to addition of another liquid (e.g., prior to the addition of the non-aqueous polar solvent). In some cases, the mass ratio of the total mass of non-aqueous liquid(s) to the total mass of polyacrylic acid(s) is at a relatively high level when a second liquid (e.g., the non-aqueous polar solvent discussed below) is applied to the mixture. For example, in some embodiments, the mass ratio of the total mass of non-aqueous liquid(s) to the total mass of polyacrylic acid(s) is at least about 1:1 (e.g., at least about 5:1) when a second liquid (e.g., the non-aqueous polar solvent discussed below) is applied to the mixture.

In some embodiments, the time between application of the mixture to at least a portion of a substrate and a subsequent liquid application step (e.g., applying a non-aqueous polar solvent, as described below) may be relatively short. For instance, in some embodiments, the time between application of the mixture to the substrate and a subsequent method step (e.g., applying a non-aqueous polar solvent, as described below) may be less than or equal to about 20 minutes, less than or equal to about 18 minutes, less than or equal to about 16 minutes, less than or equal to about 15 minutes, less than or equal to about 14 minutes, less than or equal to about 13 minutes, or less than or equal to about 12 minutes and greater than or equal to about 5 minutes (and/or, in certain embodiments, greater than or equal to about 8 minutes, or greater than or equal to about 10 minutes). In some embodiments, a subsequent step may occur when the concentration of a component in the mixture changes by at least about 5% (e.g., at least about 50%) and/or the temperature of the mixture increases by at least about 5° C. (e.g., at least about 20° C.).

Non-limiting examples of non-aqueous liquids that may be mixed with the polyacrylic acid(s) include ethyl acetate, tetrahydrofuran, diethyl ether, dioxane, pyridine, triethylamine, benzene, p-cresol, toluene, xylene, diethyl ether, glycol, diethyl ether, petroleum ether, hexane, cyclohexane, pentane, methylene chloride, chloroform, carbon tetrachloride, dioxane, tetrahydrofuran (THF), dimethyl sulfoxide, dimethylformamide, hexamethyl-phosphoric triamide, pyridine, triethylamine, picoline, and mixtures thereof. In some embodiments, the non-aqueous liquid may comprise ethyl acetate.

As noted above, in some embodiments, the step of establishing (e.g., applying) a mixture comprising polyacrylic acid(s) and non-aqueous liquid(s) can be followed by a liquid displacement step. In some embodiments, the displacement step may include applying a non-aqueous polar solvent (e.g., ethanol) to the mixture on the substrate. In some cases, the non-aqueous polar solvent may serve to displace at least a portion of the non-aqueous liquid and/or disrupt the association between at least a portion of the polyacrylic acid molecules and the non-aqueous liquid molecules and/or promote interaction between certain matrix components (e.g., one or more polyacrylic acids). In certain embodiments, the displacement step may facilitate the arrangement of the polyacrylic acid(s) in the mixture and/or evaporation of the non-aqueous liquid and/or non-aqueous polar solvent. For instance, the non-aqueous polar solvent may facilitate interaction between matrix component(s) in the mixture. As another example, the non-aqueous polar solvent may facilitate hydrogen bonding between polyacrylic acid molecules in the mixture. The hydrogen bonding may contribute to the formation of a cohesive matrix, according to certain embodiments.

As used herein, the term "non-aqueous polar solvent" refers to a polar solvent that is not water. In some embodiments, the non-aqueous polar solvent solvates at least a portion of the polyacrylic acid molecules in the mixture. In certain embodiments, the non-aqueous polar solvent is a liquid.

As used herein, the term "polar solvent" refers to a solvent having a dielectric constant of greater than about 5. In some instances, the polar solvent may have a dielectric constant greater than about 5 and less than or equal to about 300. The dielectric constant may be measured at 20° C. using methods known in the art. Dielectric constants for solvents can be found in, e.g., the CRC Handbook of Chemistry and Physics. 96th ed. CRC Press: Boca Raton, Fla., 2015-2016.

A relatively low amount of water may be present in the mixture prior to, during, and/or after the addition of the non-aqueous polar solvent. For instance, in some embodiments, the amount of water present in the mixture prior to, during, and/or after the addition of the non-aqueous solvent may be less than or equal to about 10 wt. %, less than or equal to about 8 wt. %, less than or equal to about 6 wt. %, less than or equal to about 5 wt. %, less than or equal to about 2 wt. %, less than or equal to about 1 wt. %, less than or equal to about 0.5 wt. %, less than or equal to about 0.1 wt. %, less than or equal to about 0.05 wt. %, or less than or equal to about 0.01 wt. % of the mixture. In some instances, water may not be present in the mixture prior to, during, and/or after the addition of the non-aqueous polar solvent.

In some embodiments, the mass ratio of total amounts of non-aqueous polar solvent(s) to total mass of the mixture to which it is applied may be relatively low. For instance, in some embodiments, the mass ratios of total amounts of non-aqueous polar solvent(s) to total mass of the mixture to which it is applied may be less than or equal to about 1:1, less than or equal to about 1:1.2, less than or equal to about 1:1.5, less than or equal to about 1:2, less than or equal to about 1:3, less than or equal to about 1:4, less than or equal to about 1:5, less than or equal to about 1:6, less than or equal to about 1:8, or less than or equal to about 1:10. In some instances, the mass ratio of the total mass of polyacrylic acid(s) to the total mass of non-aqueous liquid(s) within the mixture is greater than or equal to about 1:10, greater than or equal to about 1:9, greater than or equal to about 1:8, greater than or equal to about an 1:6, greater than or equal to about 1:5, greater than or equal to about 1:4, greater than or equal to about 1:3, greater than or equal to about 1:2, greater than or equal to about 1:1.5, or greater than or equal to about 1:1.2. Combinations of the above-referenced ranges are also possible (e.g., greater than or equal to about 1:10 and less than or equal to about 1:1).

In general, the non-aqueous polar solvent may be applied to the mixture using any suitable technique. For instance, in some embodiments, the non-aqueous polar solvent may be applied to the mixture via spray coating, misting, casting, spin coating, and/or dip coating. According to certain embodiments, the non-aqueous polar solvent can be sprayed onto the substrate, for example, using any of the methods and/or parameters described below with respect to the spraying of a mixture of at least one non-aqueous solvent and at least one polyacrylic acid. In some embodiments, the non-aqueous polar solvent may be applied to the mixture in a manner that allows a relatively large percentage of the exposed surface of the mixture to be exposed to the non-aqueous polar solvent. For instance, the percent exposed surface area of mixture that is exposed to the non-aqueous polar solvent may be greater than or equal to about 50%, greater than or equal to about 60%, greater than or equal to about 70%, greater than or equal to about 80%/o, greater than or equal to about 90%, greater than or equal to about 95%, greater than or equal to about 96%, greater than or equal to about 97%, greater than or equal to about 98%, or greater than or equal to about 99%.

In some embodiments, the time between application of the non-aqueous polar solvent to the mixture and a subsequent method step (such as liquid removal, e.g., via drying), may be relatively short. For instance, in some embodiments, the time between application to the substrate and a subsequent method step may be less than or equal to about 15 minutes, less than or equal to about 12 minutes, less than or equal to about 10 minutes, less than or equal to about 8 minutes, less than or equal to about 6 minutes, less than or equal to about 5 minutes, or less than or equal to about 4 minutes and greater than or equal to about 1 minutes (e.g., greater than or equal to about 2 minutes). In some embodiments, a subsequent step may occur when the concentration of a component in the mixture changes by at least about 5% (e.g., at least about 50%) and/or the temperature of the mixture increases by at least about 5° C. (e.g., at least about 20° C.).

Non-limiting examples of non-aqueous polar solvents that may be applied to the mixtures of polyacrylic acid(s) and non-aqueous liquid(s) described herein include but are not limited to polar aprotic solvents (e.g., dichloromethane (DCM), tetrahydrofuran (THF), ethyl acetate, acetone, dimethylformamide (DMF), acetonitrile, dimethyl sulfoxide (DMSO), and propylene carbonate) and polar protic solvents (e.g., formic acid, n-butanol, isopropanol, n-propanol, ethanol, methanol, acetic acid, nitromethane, sugar alcohols, non-ionic surfactants), and mixtures thereof. The non-aqueous polar solvent can comprise, according to certain embodiments, an organic solvent. In certain embodiments, the non-aqueous polar solvent comprises an alcohol. The non-aqueous polar solvent comprises, in some embodiments, at least one of methanol, ethanol, and propanol (e.g., isopropanol). In certain, but not necessarily all embodiments, it can be advantageous to use a non-aqueous polar solvent comprising ethanol as the non-aqueous polar solvent. In some embodiments, the non-aqueous polar solvent comprises ethanol and methanol. In some embodiments, the non-aqueous polar solvent comprises propanol (e.g., isopropanol). In some embodiments, the non-aqueous polar solvent comprises butanol.

In some embodiments, certain additives may be applied to the mixture on the substrate prior to, along with, and/or subsequent to the addition of the non-aqueous solvent. For example, glycerol may be applied to the mixture on the substrate along with the non-aqueous polar solvent (e.g., ethanol). Non-limiting examples of suitable additives include glycerol, polyethylene glycol, polysorbate, and sugar alcohols.

In some embodiments, the total weight percentage of additives in the mixture (e.g., prior to, during, and/or after addition of the non-aqueous polar solvent) may be relatively small. For instance, the total weight percentage of the additives in the mixture be less than or equal to about 10 wt. %, less than or equal to about 8 wt. %, less than or equal to about 6 wt. %, less than or equal to about 5 wt. %, less than or equal to about 4 wt. %, less than or equal to about 3 wt. %, less than or equal to about 2 wt. %, less than or equal to about 1 wt. %, less than or equal to about 0.5 wt. %, or less than or equal to about 0.1 wt. %. In some instances, the weight percentage may be greater than or equal to about 0.01 wt. %, greater than or equal to about 0.05 wt. %, greater than or equal to about 0.1 wt. %, greater than or equal to about 0.5 wt. %, greater than or equal to about 1 wt. %, greater than or equal to about 2 wt. %, greater than or equal to about 3 wt. %, greater than or equal to about 4 wt. %, greater than or equal to about 5 wt. %, greater than or equal to about 6 wt. %, or greater than or equal to about 8 wt. %. Combinations of the above referenced ranges are also possible (e.g., greater than or equal to 0.01 wt. % and less than or equal to about 10 wt. %)

In some embodiments, at least a portion of (and, in many instances, a relatively large percentage of) the non-aqueous liquid and/or the non-aqueous polar solvent may be removed (e.g., via evaporation) to produce the adhesive matrix. In some embodiments, after the removal step, the amount of residual solvent (i.e., liquid remaining from prior method steps) may be relatively low. For instance, according to certain embodiments, after at least a portion of the non-aqueous liquid and/or the non-aqueous polar solvent have been removed, the sum of the amount of the non-aqueous liquid and the non-aqueous polar solvent in the adhesive matrix is less than or equal to about 8 wt. % (e.g., less than or equal to about 5 wt. %, less than or equal to about 3 wt. %, less than or equal to about 1 wt. %, less than or equal to about 0.5 wt. %, or less than or equal to about 0.1 wt. %). Evaporation of the non-aqueous liquid and/or the non-aqueous polar solvent may result in the formation of an adhesive matrix, such as an adhesive film. The adhesive matrix may have beneficial properties due in part to the interaction between matrix components induced, in part, by dispersion and/or displacement processes described above. For example, in some cases, the adhesive matrix may have a cohesive structure. In some cases, the adhesive matrix may be self-supporting, and optionally flexible and/or elastic. In some cases, the adhesive matrix may be cross-linked.

In general, any suitable liquid removal method may be used to remove the non-aqueous liquid and/or non-aqueous polar solvent. For instance, the liquid may be removed by applying energy (e.g., thermal energy) to induce evaporation. In some cases, the liquid may be removed via evaporation without the substantial application of energy by a user.

As used herein, the term "residual solvent" refers to the amount of liquid (e.g., non-aqueous liquid and non-aqueous polar solvent) used in the fabrication of the adhesive matrix that remains in the adhesive matrix after the liquid removal step.

In some embodiments, the weight percentage of the sum of the non-aqueous liquid(s) and the non-aqueous polar solvent(s) in the adhesive matrix and/or composition after the liquid removal (e.g., evaporation) step may be less than or equal to about 8 wt. %, less than or equal to about 5 wt. %, less than or equal to about 4 wt. %, less than or equal to about 3 wt. %, less than or equal to about 2 wt. %, less than or equal to about 1 wt. %, less than or equal to about 0.5 wt. %, less than or equal to about 0.1 wt. %, less than or equal to about 0.05 wt. %, less than or equal to about 0.01 wt. %, less than or equal to about 0.005 wt. %, less than or equal to about 0.001 wt. %, or less than or equal to about 0.0005 wt. %. In some instances, the weight percentage may be greater than or equal to about 0.0001 wt. %, greater than or equal to about 0.0005 wt. %, greater than or equal to about 0.001 wt. %, greater than or equal to about 0.005 wt. %, greater than or equal to about 0.01 wt. %, greater than or equal to about 0.05 wt. %, greater than or equal to about 0.1 wt. %, or greater than or equal to about 0.5 wt. %. Combinations of the above referenced ranges are also possible (e.g., greater than or equal to 0.001 wt. % and less than or equal to about 8 wt. %, greater than or equal to 0.001 wt. % and less than or equal to about 3 wt. %, greater than or equal to 0.0001 wt. % and less than or equal to about 1 wt. %, greater than or equal to 0.0001 wt. % and less than or equal to about 0.1 wt. %). In embodiments in which more than one type of liquid (e.g., non-aqueous polar solvent, non-aqueous liquid) is present in the adhesive matrix, each type of liquid (e.g., non-aqueous polar solvent, non-aqueous liquid) may independently have a weight percentage with respect to the adhesive matrix in one or more of the ranges described above, provided that the total percentage is less than or equal to about 5 wt. %.

In general, the method is performed with minimal use of water. For instance, in some embodiments, the amount of water in the mixture at any point during the method may be less than or equal to about 10 wt. %, less than or equal to about 8 wt. %, less than or equal to about 6 wt. %, less than or equal to about 5 wt. %, less than or equal to about 2 wt. %, less than or equal to about 1 wt. %, less than or equal to about 0.5 wt. %, less than or equal to about 0.1 wt. %, less than or equal to about 0.05 wt. %, or less than or equal to about 0.01 wt. %.

It has been discovered that, according to certain, although not necessarily all embodiments, the use of a mixture of a first polyacrylic acid cross-linked with pentaerythritol and/or allyl sucrose and a second polyacrylic acid cross-linked with divinyl glycol can lead to the production of adhesive matrices with enhanced adhesive and/or mechanical properties. In some such embodiments, the properties of the resultant adhesive matrix are further enhanced when low amounts of water are used during processing. Accordingly, in some embodiments, a method of forming the adhesive matrix comprises applying a mixture comprising a non-aqueous liquid, a first polyacrylic acid cross-linked with pentaerythritol and/or allyl sucrose, and a second polyacrylic acid cross-linked with divinyl glycol to a substrate, wherein the amount of water in the mixture is less than or equal to about 2 wt. %. It has also been discovered that the use of ethanol as a non-aqueous polar solvent can be particularly advantageous, according to certain although not necessarily all embodiments. Accordingly, in some embodiments, a non-aqueous polar solvent containing ethanol in an amount of at least about 90 wt. % may be applied to the mixture on the substrate and at least a portion of the non-aqueous liquid and the non-aqueous polar solvent may be allowed to evaporate to produce the adhesive matrix. In some such embodiments, after the evaporation, the sum of the amount of the non-aqueous liquid and the non-aqueous polar solvent in the adhesive matrix is between about 0.001 wt. % and about 3 wt. % (or, in some embodiments, between about 0.001 wt. % and about 2 wt. %, or between about 0.001 wt. % and about 1 wt. %).

In another aspect, a method is provided in which an adhesive matrix is formed by spraying a mixture comprising at least one non-aqueous solvent and at least one polyacrylic acid onto a substrate. Those of ordinary skill in the art are familiar with spraying, which generally involves applying a force to a liquid such that droplets are directed from the source. In some embodiments, the spraying comprises using an apparatus to form droplets of a mixture of at least one non-aqueous solvent and at least one polyacrylic acid, such that the droplets of the mixture are directed toward and deposited on a substrate.

Figure 1B:
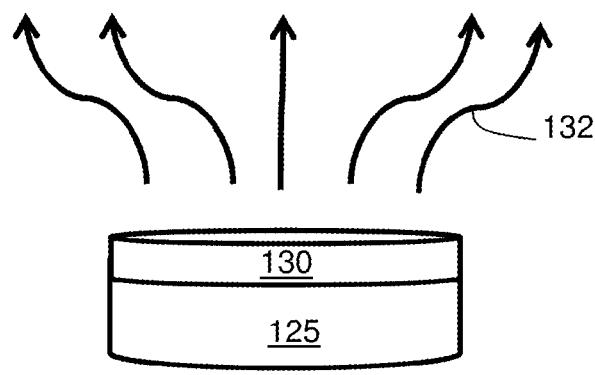
Figure 1C:
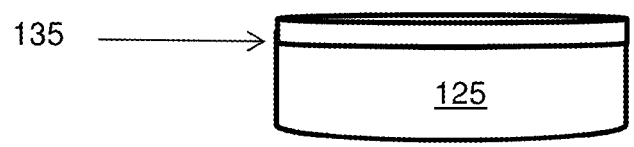

FIGS. 1A-1C are schematic illustrations showing the formation of an adhesive matrix in which spraying is employed, according to certain embodiments. As noted above, certain embodiments comprise spraying a mixture comprising at least one non-aqueous solvent and at least one polyacrylic acid onto a substrate to form a deposit of the mixture on the substrate. For example, as shown in FIG. 1A, mixture 110 (which can comprise at least one non-aqueous solvent and at least one polyacrylic acid) can be sprayed onto substrate 125. As shown in FIG. 1A, a force can be applied to mixture 110 such that droplets 115 are produced as the mixture exits source 120. Droplets 115 travel toward substrate 125, upon which droplets 115 form deposit 130.

According to certain embodiments, spraying the mixture comprises applying a pressure to the mixture and spraying the mixture through a nozzle. In some such embodiments, pressure is used to direct the mixture of the at least one non-aqueous solvent and the at least one polyacrylic acid through a nozzle. This may be achieved, according to certain embodiments, through the use of a spray gun. Upon exiting the nozzle, according to some embodiments, the mixture forms droplets which are mixed and/or atomized with air outside the nozzle (e.g., an air cap of the nozzle) before deposition of the droplets on the substrate. In some embodiments, nozzle pressure and/or mixture viscosity can be adjusted to ensure proper atomization and/or formation of substantially uniform coatings. In certain cases, the sprayed droplets have a size that varies inversely with atomization pressure. In some cases, the sprayed droplets form a coating which has a thickness that increases with solution concentration. Examples of suitable pressure-based spray systems include those manufactured by Gapptec.

In some embodiments, spraying the mixture comprises electrospraying the mixture. Those of ordinary skill in the art are familiar with electrospraying, which refers to a process in which an electric potential is established between the source of the droplets and the substrate onto which the droplets are projected. The electric potential can exert a force on the mixture, which can result in the formation of droplets from the mixture. Accordingly, in some embodiments, droplets of the mixture of the non-aqueous solvent(s) and the polyacrylic acid(s) can be transferred from a source of the mixture to the substrate across a difference in electrical potential. In some such embodiments, a high voltage is used to negatively charge the mixture such that its droplets accelerate toward a grounded substrate. In some cases, the use of electrospraying may help increase the efficiency with which the mixture is transferred to the substrate. Electrospraying can, in some cases, help reduce residual solvent levels in the final adhesive composition. As one particular example, a 1.7% solution of polyacrylic acid in ethanol has been successfully electrosprayed using by applying an electric potential differential of 2.6 kV. These conditions yielded a polyacrylic acid-based coating having a weight of approximately 6 mg/cm$^2$, a residual solvent level under 1 wt. % and an adhesive burst strength of 977 mmHg gauge (1737 mmHg absolute).

It should be understood that spraying is not limited to pressure-based spraying and electrospraying, and in other embodiments, other methods of spraying the mixture could be employed.

According to certain embodiments, at least a portion of the at least one non-aqueous solvent is evaporated from the deposit to produce the adhesive matrix. For example, in FIG. 1B, non-aqueous solvent can be evaporated from deposit 130 (e.g., via arrows 132). In some such embodiments, the portion of the deposit that is left behind on the substrate can form at least a portion of the adhesive matrix. For example, FIG. 1C shows adhesive matrix 135, which is produced after non-aqueous solvent has been evaporated from deposit 130.

In some embodiments, the evaporation of non-aqueous solvent occurs over a period of time long enough to allow for both complete or substantially complete evaporation of the solvent as well as complete or substantially complete solvation of the polyacrylic acid during the drying process. This can, according to certain embodiments, ensure that a film is not first formed at the top of the deposit. In some cases, if a film forms at the top of a deposit, the film can form a barrier to solvent transport which can trap residual solvent inside the interior of the deposit and/or at the interface between the substrate and the deposit, which can negatively affect the properties of the final adhesive matrix. The efficiency of solvent removal by evaporation can be affected by the amount of time over which it occurs, the air circulation present, the ambient temperature, ambient pressure, and/or ambient humidity, among other factors.

According to certain embodiments in which a mixture of at least one non-aqueous solvent and at least one polyacrylic acid is sprayed onto the substrate, the mixture may include a relatively large amount of the non-aqueous solvent(s). In some embodiments, the mixture contains the at least one non-aqueous solvent in an amount of at least about 50 wt. %, at least about 60 wt. %, at least about 75 wt. %, at least about 90 wt. %, at least about 95 wt. %, or at least about 98 wt. %. In some embodiments, the mixture contains the at least one non-aqueous solvent in an amount of less than or equal to about 99.9 wt. %, less than or equal to about 99 wt. %, less than or equal to about 98 wt. %, less than or equal to about 95 wt. %, less than or equal to about 90 wt. %, less than or equal to about 85 wt. %, less than or equal to about 80 wt. %, or less than or equal to about 75 wt. %. Combinations of the above-referenced ranges are also possible (e.g. from about 50 wt. % to about 99.9 wt. %). Other ranges are also possible.

According to certain embodiments in which a mixture of at least one non-aqueous solvent and at least one polyacrylic acid is sprayed onto the substrate, the non-aqueous solvent component of the mixture may comprise any suitable non-aqueous solvent, including any of the non-aqueous solvents described elsewhere herein. In some embodiments, the at least one non-aqueous solvent comprises a non-aqueous polar solvent, including any of the non-aqueous polar solvents described elsewhere herein. In some embodiments, the at least one non-aqueous solvent comprises at least one alcohol. In some such embodiments, the at least one alcohol comprises at least one of methanol, ethanol, propanol, and butanol. Non-aqueous solvents which comprise blends of the above-mentioned solvents are also possible (e.g., isopropanol and ethanol).

According to certain embodiments in which a mixture of at least one non-aqueous solvent and at least one polyacrylic acid is sprayed onto the substrate, the non-aqueous solvent component of the mixture may contain a relatively large amount of at least one alcohol. In some embodiments, the alcohol content of the solvent component of the mixture is at least about 50 wt. %, at least about 60 wt. %, at least about 75 wt. %, at least about 90 wt. %, at least about 95 wt. %, or at least about 98 wt. %. In some embodiments, the mixture contains the at least one non-aqueous solvent in an amount of less than or equal to about 99.9 wt. %, less than or equal to about 99 wt. %, less than or equal to about 98 wt. %, less than or equal to about 95 wt. %, less than or equal to about 90 wt. %, less than or equal to about 85 wt. %, less than or equal to about 80 wt. %, or less than or equal to about 75 wt. %. Combinations of the above-referenced ranges are also possible (e.g. from about 50 wt. % to about 99.9 wt. %). Other ranges are also possible. It should be understood that, to calculate the alcohol content of a mixture, the weight percentages of each alcohol (e.g., methanol, ethanol, propanol, butanol, etc.) are added together.

According to certain embodiments in which a mixture of at least one non-aqueous solvent and at least one polyacrylic acid is sprayed onto the substrate, the non-aqueous solvent component of the mixture may contain a relatively large amount of methanol, ethanol, propanol, and/or butanol. In some embodiments, the total amount of methanol, ethanol, propanol, and butanol in the solvent component of the mixture is at least about 50 wt. %, at least about 60 wt. %, at least about 75 wt. %, at least about 90 wt. %, at least about 95 wt. %, or at least about 98 wt. %. In some embodiments, the total amount of methanol, ethanol, propanol, and butanol in the solvent component of the mixture is less than or equal to about 99 wt. %, less than or equal to about 98 wt. %, less than or equal to about 95 wt. %, less than or equal to about 90 wt. %, less than or equal to about 85 wt. %, less than or equal to about 80 wt. %, or less than or equal to about 75 wt. %. Combinations of the above-referenced ranges are also possible (e.g. from about 50 wt. % to about 99 wt. %). Other ranges are also possible. It should be understood that, to calculate the total amount of methanol, ethanol, propanol, and butanol in a mixture, the weight percentages of each of these alcohols are added together.

According to certain embodiments in which a mixture of at least one non-aqueous solvent and at least one polyacrylic acid is sprayed onto the substrate, the non-aqueous solvent component of the mixture may contain a relatively large amount of ethanol and/or propanol. In some embodiments, the total amount of ethanol and propanol in the solvent component of the mixture is at least about 50 wt. %, at least about 60 wt. %, at least about 75 wt. %, at least about 90 wt. %, at least about 95 wt. %, or at least about 98 wt. %. In some embodiments, the total amount of ethanol and propanol in the solvent component of the mixture is less than or equal to about 99 wt. %, less than or equal to about 98 wt. %, less than or equal to about 95 wt. %, less than or equal to about 90 wt. %, less than or equal to about 85 wt. %, less than or equal to about 80 wt. %, or less than or equal to about 75 wt. %. Combinations of the above-referenced ranges are also possible (e.g. from about 50 wt. % to about 99 wt. %). Other ranges are also possible.

According to certain embodiments in which a mixture of at least one non-aqueous solvent and at least one polyacrylic acid is sprayed onto the substrate, the non-aqueous solvent component of the mixture may contain a relatively large amount of propanol. In some embodiments, the solvent component of the mixture contains propanol (e.g., isopropanol) in an amount of at least about 50 wt. %, at least about 60 wt. %, at least about 75 wt. %, at least about 90 wt. %, at least about 95 wt. %, or at least about 98 wt. %. In some embodiments, the solvent component of the mixture contains propanol (e.g., isopropanol) in an amount of less than or equal to about 99 wt. %, less than or equal to about 98 wt. %, less than or equal to about 95 wt. %, less than or equal to about 90 wt. %, less than or equal to about 85 wt. %, less than or equal to about 80 wt. %, or less than or equal to about 75 wt. %. Combinations of the above-referenced ranges are also possible (e.g. from about 50 wt. % to about 99 wt. %). Other ranges are also possible.

According to certain embodiments in which a mixture of at least one non-aqueous solvent and at least one polyacrylic acid is sprayed onto the substrate, the non-aqueous solvent component of the mixture may contain a relatively large amount of ethanol. In some embodiments, the solvent component of the mixture contains ethanol in an amount of at least about 50 wt. %, at least about 60 wt. %, at least about 75 wt. %, at least about 90 wt. %, at least about 95 wt. %, or at least about 98 wt. %. In some embodiments, the solvent component of the mixture contains ethanol in an amount of less than or equal to about 99 wt. %, less than or equal to about 98 wt. %, less than or equal to about 95 wt. %, less than or equal to about 90 wt. %, less than or equal to about 85 wt. %, less than or equal to about 80 wt. %, or less than or equal to about 75 wt. %. Combinations of the above-referenced ranges are also possible (e.g. from about 50 wt. % to about 99 wt. %). Other ranges are also possible.

According to certain embodiments in which a mixture of at least one non-aqueous solvent and at least one polyacrylic acid is sprayed onto the substrate, the mixture contains a relatively low amount of water (or no water). For instance, in some embodiments, the amount of water in the mixture may be less than or equal to about 10 wt. %, less than or equal to about 8 wt. %, less than or equal to about 6 wt. %, less than or equal to about 5 wt. %, less than or equal to about 2 wt. %, less than or equal to about 1 wt. %, less than or equal to about 0.5 wt. %, less than or equal to about 0.1 wt. %, less than or equal to about 0.05 wt. %, or less than or equal to about 0.01 wt. %.

In some embodiments in which a mixture of at least one non-aqueous solvent and at least one polyacrylic acid is sprayed onto the substrate, a variety of suitable polyacrylic acids may be used. In some embodiments, the at least one polyacrylic acid comprises a non-crosslinked polyacrylic acid. In some embodiments, the at least one polyacrylic acid comprises a polyacrylic acid crosslinked with pentaerythritol and/or allyl sucrose. In certain embodiments, the at least one polyacrylic acid comprises a polyacrylic acid crosslinked with divinyl glycol. The at least one polyacrylic acid could also comprise, in addition to or in place of these, any of the polyacrylic acids described in more detail below or elsewhere herein.

In certain embodiments in which a mixture of at least one non-aqueous solvent and at least one polyacrylic acid is sprayed onto the substrate, the mixture of non-aqueous solvent and at least one polyacrylic acid may include a variety of suitable concentrations of polyacrylic acid. In some embodiments, the mixture contains the at least one polyacrylic acid in an amount of greater than or equal to 0.1 wt. %, greater than or equal to about 0.5 wt. %, greater than or equal to about 1 wt. %, greater than or equal to about 2 wt. %, greater than or equal to about 5 wt. %, greater than or equal to about 7.5 wt. %, greater than or equal to about 10 wt. %, greater than or equal to about 12.5 wt. %, or greater than or equal to about 15 wt. %. In some embodiments, the mixture contains the at least one polyacrylic acid in an amount of less than or equal to about 25 wt. %, less than or equal to about 22.5 wt. %, less than or equal to about 20 wt. %, less than or equal to about 17.5 wt. %, less than or equal to about 15 wt. %, or less than or equal to about 12.5 wt. %. Combinations of the above-referenced ranges are also possible (e.g. from about 0.1 wt. % to about 25 wt. %, from about 1 wt. % to about 25 wt. %). Other ranges are also possible. It should be understood that, when more than one polyacrylic acid is present, the amount of the at least one polyacrylic acid in the mixture is determined by adding the weight percentages of each of the polyacrylic acids.

The mixture of the at least one polyacrylic acid and the at least one non-aqueous solvent can be made by a variety of suitable methods. In some embodiments, the mixture is fabricated by adding particles comprising the at least one polyacrylic acid to the at least one non-aqueous solvent. In some such embodiments, at least a portion (e.g., at least about 50 wt. %, at least about 75 wt. %, at least about 90 wt. %, at least about 95 wt. %, or at least about 98 wt. %) of the particles have maximum cross-sectional dimensions of less than about 10 microns or less than about 5 microns. In some embodiments, at least a portion (e.g., at least about 50 wt. %, at least about 75 wt. %, at least about 90 wt. %, at least about 95 wt. %, or at least about 98 wt. %) of the particles have maximum cross-sectional dimensions of at least about 0.001 microns, at least about 0.01 microns, or at least about 0.1 microns. Combinations of the above-referenced ranges are also possible (e.g. greater than about 0.001 microns and less than about 10 microns). Other ranges are also possible.

The mixture of non-aqueous solvent(s) and polyacrylic acid(s) may be mixed for any suitable amount of time prior to being sprayed. The solvent viscosity typically increases after mixing to an extent that generally depends on the chain length and crosslinking of the polyacrylic acid and on the non-aqueous solvent component of the mixture. For example, in some cases, mixture compositions can thicken after 20 minutes and become too thick to be poured after 12 hours. In some embodiments, the mixture may be mixed for a period of time greater than or equal to about 2 minutes, greater than or equal to about 5 minutes, greater than or equal to about 10 minutes, greater than or equal to about 20 minutes, greater than or equal to about 30 minutes, greater than or equal to about 60 minutes, greater than or equal to about 2 hours, or greater than or equal to about 4 hours. In some embodiments, the mixture may be mixed for a period of time of less than or equal to about 8 hours, less than or equal to about 6 hours, less than or equal to about 4 hours, less than or equal to about 2 hours, less than or equal to about 60 minutes, less than or equal to about 10 minutes, or less than or equal to about 2 minutes. Combinations of the above-referenced ranges are also possible (e.g. greater than or equal to about 2 minutes and less than or equal to about 8 hours). Other ranges are also possible.

A variety of nozzles may be used to spray the mixture, according to certain embodiments in which pressure is used as a driving force. Nozzle sizes may be chosen, in some cases, such that they are large enough to prevent clogging and small enough to form a coating without excess solvent and/or with a desired evaporation time. In some embodiments, the nozzle comprises an opening with a maximum cross-sectional dimension of from about 0.5 mm to about 2 mm. In some embodiments, the opening of the nozzle is at least about 0.5 mm, at least about 0.6 mm, at least about 0.7 mm, at least about 0.8 mm, at least about 0.9 mm, at least about 1.0 mm, at least about 1.1 mm, at least about 1.2 mm, at least about 1.3 mm, at least about 1.4 mm, at least about 1.5 mm, or at least about 1.6 mm. In some embodiments, the opening of the nozzle is less than or equal to about 2.0 mm, less than or equal to about 1.9 mm, less than or equal to about 1.8 mm, or less than or equal to about 1.7 mm. Combinations of the above-referenced ranges are also possible. Other ranges are also possible.

The pressure used to spray the mixture of non-aqueous solvent(s) and polyacrylic acid(s) (when pressure-driven spraying is employed) may be any suitable value. Mixtures of higher viscosity generally require larger pressures, all other factors being equal. In some embodiments, the pressure may be greater than or equal to about 15 pounds per square inch gauge (psig), greater than or equal to about 20 psig, greater than or equal to about 30 psig, greater than or equal to about 35 psig, greater than or equal to about 40 psig, greater than or equal to about 45 psig, greater than or equal to about 50 psig, or greater than or equal to about 60 psig. In some embodiments, the pressure may be less than or equal to about 65 psig, less than or equal to about 60 psig, less than or equal to about 50 psig, less than or equal to about 45 psig, or less than or equal to about 42 psig. Combinations of the above-referenced ranges are also possible (e.g. greater than or equal to about 15 psig and less than or equal to about 65 psig). Other ranges are also possible.

In certain embodiments in which a mixture of at least one non-aqueous solvent and at least one polyacrylic acid is sprayed onto the substrate, the flow rate of the mixture (e.g., through the nozzle in the case of pressure-driven flow, or from the source in the case of electrospraying) may fall within a number of suitable ranges. In some embodiments, during the spraying, the volumetric flow rate of the mixture (from the source to the substrate) is from about 10 to about 50 mL/min. In certain embodiments, during the spraying, the volumetric flow rate may be greater than or equal to about 10 mL/minute, greater than or equal to about 15 mL/minute, greater than or equal to about mL/minute, greater than or equal to about 25 mL/minute, greater than or equal to about 30 mL/minute, greater than or equal to about 35 mL/minute, greater than or equal to about 40 mL/minute, or greater than or equal to about 45 mL/minute. In some embodiments, the flow rate may be less than or equal to about 50 mL/minute, less than or equal to about 45 mL/minute, less than or equal to about 40 mL/minute, less than or equal to about 35 mL/minute, less than or equal to about 30 mL/minute, less than or equal to about 25 mL/minute, less than or equal to about 20 mL/minute, or less than or equal to about 15 mL/minute. Combinations of the above-referenced ranges are also possible. Other ranges are also possible.

The droplets formed during the spraying process may be of a variety of suitable morphologies and/or sizes. In some embodiments, the droplets can be spherical or substantially spherical. In some embodiments, the spraying produces droplets of the mixture having maximum cross-sectional dimensions of from about 2 microns to about 100 microns. In some embodiments, at least a portion (e.g., at least about 50 wt. %, at least about 75 wt. %, at least about 90 wt. %, at least about 95 wt. %, or at least about 98 wt. %) of the droplets have a maximum cross-sectional dimension of at least about 2 microns, at least about 3 microns, at least about 4 microns, at least about 5 microns, at least about 6 microns, at least about 7 microns, at least about 8 microns, at least about 9 microns, at least about 10 microns, at least about 15 microns, at least about 25 microns, or at least about 35 microns. In some embodiments, at least a portion (e.g., at least about 50 wt. %, at least about 75 wt. %, at least about 90 wt. %, at least about 95 wt. %, or at least about 98 wt. %) of the droplets have a maximum cross-sectional dimension of less than about 100 microns, less than about 90 microns, less than about 80 microns, less than about 70 microns, or less than about 65 microns. Combinations of the above-referenced ranges are also possible. Other ranges are also possible. The maximum cross-sectional dimension of a droplet is the largest dimension that passes from one external boundary of the droplet to another external boundary of the droplet. Those of ordinary skill in the art would be capable of determining the maximum cross-sectional dimension of a droplet by examining a magnified image of the droplet.

In certain embodiments in which a mixture of at least one non-aqueous solvent and at least one polyacrylic acid is sprayed onto the substrate, the source of the droplets and the substrate can be positioned relative to each other to achieve a desired separation distance. In some embodiments, the distance between the source of the droplets and the substrate can be at least about 2 inches, at least about 3 inches, at least about 5 inches, at least about 10 inches, or at least about 15 inches. In some embodiments, the distance between the source of the droplets and the substrate can be about 24 inches or less. Combinations of these ranges are also possible (e.g., from about 2 inches to about 24 inches). Other ranges are also possible. It should be understood that the distance between the source and the substrate corresponds to the shortest linear distance between the source and the substrate.

Spraying may comprise any suitable number of passes of the source (e.g., nozzle) over the substrate. In some embodiments, the source may make at least 1 pass, at least 2 passes, at least 3 passes, at least 4 passes, at least 5 passes, at least 6 passes, at least 7 passes, at least 8 passes, at least 9 passes, at least 10 passes, at least 11 passes, at least 12 passes, at least 13 passes, at least 14 passes, at least 15 passes, or more.

Spraying may occur over any suitable time period. In some embodiments, spraying may occur over a period of time greater than or equal to about 1 minute, greater than or equal to about 2 minutes, greater than or equal to about 5 minutes, greater than or equal to about 10 minutes, greater than or equal to about 20 minutes, greater than or equal to about 30 minutes, greater than or equal to about 45 minutes, greater than or equal to about 1 hour, greater than or equal to about 2 hours, greater than or equal to about 3 hours, or greater than or equal to about 4 hours. In some embodiments, the spraying may occur over a period of time less than or equal to about 4 hours, less than or equal to about 3.5 hours, less than or equal to about 3 hours, less than or equal to about 2.5 hours, less than or equal to about 2 hours, less than or equal to about 1.5 hours, less than or equal to about 1 hour, less than or equal to about 45 minutes, less than or equal to about 30 minutes, less than or equal to about 20 minutes, less than or equal to about 15 minutes, less than or equal to about 10 minutes, or less than or equal to about 5 minutes. Combinations of the above-referenced ranges are also possible (e.g. greater than or equal to about 1 minute and less than or equal to about 4 hours). Other ranges are also possible.

The deposit may have any suitable mass. In some embodiments, the amount of deposit formed over the substrate may be greater than or equal to about 2 mg/cm$^2$, greater than or equal to about 5 mg/cm$^2$, greater than or equal to about 6 mg/cm$^2$, greater than or equal to about 7.5 mg/cm$^2$, greater than or equal to about 10 mg/cm$^2$, greater than or equal to about 12.5 mg/cm$^2$, greater than or equal to about 15 mg/cm$^2$, greater than or equal to about 17.5 mg/cm$^2$, greater than or equal to about 20 mg/cm$^2$, greater than or equal to about 25 mg/cm$^2$, greater than or equal to about 30 mg/cm$^2$, or greater than or equal to about 35 mg/cm$^2$. In some embodiments, the amount of deposit formed over the substrate may be less than or equal to about 1000 mg/cm$^2$, less than or equal to about 500 mg/cm$^2$, or less than or equal to about 300 mg/cm$^2$. Combinations of the above-referenced ranges are also possible (e.g. greater than or equal to about 2 mg/cm$^2$ and less than or equal to about 1000 mg/cm$^2$). Other ranges are also possible. To calculate the mass of a material (e.g., a deposit, an adhesive matrix) that has been formed over a substrate, one divides the mass of the material by the area of the substrate over which the material has been formed. For example, if 2 mg of deposit has been formed over a 0.5 cm$^2$ facial area of the substrate, the mass of the deposit formed over the substrate is 4 mg/cm$^2$ (i.e., 2 mg divided by 0.5 cm$^2$).

The adhesive matrix may be formed by spraying on a number of suitable substrates, including any of the substrates described elsewhere herein. In some embodiments, the substrate comprises small intestinal submucosa and/or fibrin. Other substrates are also possible.

Evaporation of the at least one non-aqueous solvent from the deposit to form the adhesive matrix may occur under any suitable conditions. In some embodiments, at least a portion of the evaporation occurs under ambient conditions.

In some embodiments, at least a portion of the evaporation occurs at an ambient temperature greater than or equal to about 80° F., greater than or equal to about 90° F., or greater than or equal to about 100° F. In some embodiments, at least a portion of the evaporation occurs at an ambient temperature of less than or equal to about 140° F., less than or equal to about 130° F., less than or equal to about 120° F., or less than or equal to about 110° F. Combinations of the above-referenced ranges are also possible (e.g., at an ambient temperature between about 80° F. and about 140° F. Other ranges are also possible.

In some embodiments, at least a portion of the evaporation occurs at an absolute ambient pressure that is below 1 atmosphere (e.g., at an absolute ambient pressure of about 0.95 atm or less, about 0.9 atm or less, about 0.8 atm or less, about 0.7 atm or less, about 0.6 atm or less, about 0.5 atm or less, or lower).

The adhesive matrix that is made by spraying the mixture of at least one non-aqueous solvent and at least one polyacrylic acid may have any of the properties described below or elsewhere herein. For example, in some embodiments, the adhesive matrix may be non-covalently crosslinked. In some embodiments, the adhesive matrix may be self-supporting. Other potential properties of the adhesive matrix are described below and elsewhere herein.

The adhesive matrix may contain, according to certain embodiments, a relatively large amount of the one or more polyacrylic acids. In some embodiments, the weight percentage of polyacrylic acid in the adhesive matrix is greater than or equal to about 90 wt. %, greater than or equal to about 95 wt. %, greater than or equal to about 98 wt. %, greater than or equal to about 99 wt. %, greater than or equal to about 99.9 wt. %, or greater than or equal to about 99.99 wt. %. In some embodiments, the weight percentage of polyacrylic acid in the adhesive matrix is less than or equal to about 99.9999 wt. %, less than or equal to about 99.999 wt. %, less than or equal to about 99.99 wt. %, less than or equal to about 99.9 wt. %, less than or equal to about 99 wt. %, or less than or equal to about 98 wt. %.

In certain embodiments, after the evaporation step, the adhesive matrix may contain a relatively low amount of liquid (or it may contain substantially no liquid). Achieving a low residual liquid content (or low residual solvent content) in the adhesive matrix may produce, according to certain embodiments, a product that does not induce substantial adverse biomaterial responses (e.g., inflammation, irritation, and/or toxicity). In certain embodiments, after non-aqueous solvent is evaporated from the deposit, less than about 8 wt. %, less than or equal to about 5 wt. %, less than or equal to about 4 wt. %, less than or equal to about 3 wt. %, less than or equal to about 2 wt. %, less than or equal to about 1 wt. %, less than or equal to about 0.5 wt. %, less than or equal to about 0.1 wt. %, less than or equal to about 0.05 wt. %, less than or equal to about 0.01 wt. %, less than or equal to about 0.005 wt. %, less than or equal to about 0.001 wt. %, or less than or equal to about 0.0005 wt. % of the adhesive matrix is made up of liquid (e.g., non-aqueous solvent and/or any other liquid(s) present). In some instances, after non-aqueous solvent is evaporated from the deposit, greater than or equal to about 0.0001 wt. %, greater than or equal to about 0.0005 wt. %, greater than or equal to about 0.001 wt. %, greater than or equal to about 0.005 wt. %, greater than or equal to about 0.01 wt. %, greater than or equal to about 0.05 wt. %, greater than or equal to about 0.1 wt. %, or greater than or equal to about 0.5 wt. % of the adhesive matrix is made up of liquid. Combinations of the above referenced ranges are also possible (e.g., greater than or equal to 0.0001 wt. % and less than or equal to about 8 wt. %, greater than or equal to 0.0001 wt. % and less than or equal to about 3 wt. %, greater than or equal to 0.0001 wt. % and less than or equal to about 1 wt. %, greater than or equal to 0.0001 wt. % and less than or equal to about 0.1 wt. %).

In certain embodiments, after the evaporation step, the adhesive matrix may contain a relatively low amount of residual non-aqueous solvent (or it may contain no residual non-aqueous solvent). In certain embodiments, after non-aqueous solvent is evaporated from the deposit, less than about 8 wt. %, less than or equal to about 5 wt. %, less than or equal to about 4 wt. %, less than or equal to about 3 wt. %, less than or equal to about 2 wt. %, less than or equal to about 1 wt. %, less than or equal to about 0.5 wt. %, less than or equal to about 0.1 wt. %, less than or equal to about 0.05 wt. %, less than or equal to about 0.01 wt. %, less than or equal to about 0.005 wt. %, less than or equal to about 0.001 wt. %, or less than or equal to about 0.0005 wt. % of the adhesive matrix is made up of residual non-aqueous solvent. In some instances, after non-aqueous solvent is evaporated from the deposit, greater than or equal to about 0.0001 wt. %, greater than or equal to about 0.0005 wt. %, greater than or equal to about 0.001 wt. %, greater than or equal to about 0.005 wt. %, greater than or equal to about 0.01 wt. %, greater than or equal to about 0.05 wt. %, greater than or equal to about 0.1 wt. %, or greater than or equal to about 0.5 wt. % of the adhesive matrix is made up of residual non-aqueous solvent. Combinations of the above referenced ranges are also possible (e.g., greater than or equal to 0.0001 wt. % and less than or equal to about 8 wt. %, greater than or equal to 0.0001 wt. % and less than or equal to about 3 wt. %, greater than or equal to 0.0001 wt. % and less than or equal to about 1 wt. %, greater than or equal to 0.0001 wt. % and less than or equal to about 0.1 wt. %).

While embodiments have been described in which the adhesive matrix comprises little or no liquid or residual solvent, it should be understood that, in some embodiments, residual solvent or another liquid can remain in the adhesive matrix. In some embodiments, trace amounts of residual solvent and/or other liquids may be present in the adhesive matrix.

According to certain embodiments, the adhesive matrix may reach any of the liquid or residual solvent content levels outlined above after a relatively short period of time. In some embodiments, this time may be less than or equal to about 90 days, less than or equal to about 30 days, less than or equal to about 7 days, less than or equal to about 48 hours, less than or equal to about 24 hours, less than or equal to about 8 hours, or less than or equal to about 1 hour. In some embodiments, the time may be as little as 30 minutes, as little as 10 minutes, as little as 2 minutes, as little as 1 minute, or less. In some such embodiments, the designated level of liquid or residual solvent within the adhesive matrix may not be reached until at least 1 minute, at least 2 minutes, at least 10 minutes, or at least 30 minutes after forming the deposit on the substrate.

Accordingly, in some embodiments, at at least one point in time within 90 days (or within 30 days, within 7 days, within 48 hours, within 24 hours, within 8 hours, or within 1 hour) of forming the deposit on the substrate, less than about 8 wt. % (or less than or equal to about 5 wt. %, less than or equal to about 4 wt. %, less than or equal to about 3 wt. %, less than or equal to about 2 wt. %, less than or equal to about 1 wt. %, less than or equal to about 0.5 wt. %, less than or equal to about 0.1 wt. %, less than or equal to about 0.05 wt. %, less than or equal to about 0.01 wt. %, less than or equal to about 0.005 wt. %, less than or equal to about 0.001 wt. %, or less than or equal to about 0.0005 wt. %) of the adhesive matrix is made up of liquid. In some such embodiments, the designated level of liquid within the adhesive matrix may not be reached until at least 1 minute, at least 2 minutes, at least 10 minutes, or at least 30 minutes after forming the deposit on the substrate.

In certain embodiments, at at least one point in time within 90 days (or within 30 days, within 7 days, within 48 hours, within 24 hours, within 8 hours, or within 1 hour) of forming the deposit on the substrate, less than about 8 wt. % (or less than or equal to about 5 wt. %, less than or equal to about 4 wt. %, less than or equal to about 3 wt. %, less than or equal to about 2 wt. %, less than or equal to about 1 wt. %, less than or equal to about 0.5 wt. %, less than or equal to about 0.1 wt. %, less than or equal to about 0.05 wt. %, less than or equal to about 0.01 wt. %, less than or equal to about 0.005 wt. %, less than or equal to about 0.001 wt. %, or less than or equal to about 0.0005 wt. %) of the adhesive matrix is made up of residual non-aqueous solvent. In some such embodiments, the designated level of residual non-aqueous solvent within the adhesive matrix may not be reached until at least 1 minute, at least 2 minutes, at least 10 minutes, or at least 30 minutes after forming the deposit on the substrate.

Certain embodiments are related to adhesive matrices, which may be formed, in some cases, via certain of the methods described herein. In some embodiments, at least about 50 wt. % of the adhesive matrix is made up of at least one polyacrylic acid (e.g. a single polyacrylic acid, two polyacrylic acids, or more polyacrylic acids) and less than about 8 wt. % (e.g., less than about 5 wt. %) of the adhesive matrix is made up of liquid (e.g., water, a non-aqueous liquid, a non-aqueous polar solvent). In certain embodiments, the adhesive matrix may include at least 75 wt. % of at least one polyacrylic acid and less than about 8 wt. % (e.g., less than about 5 wt. %, between about 0.001 wt. % and 1 wt. %) liquid. In one example, the adhesive matrix comprises greater than or equal to about 90 wt. % of polyacrylic acid and less than about 5 wt. % of an alcohol, such as ethanol. The polyacrylic acid may include, according to certain embodiments, a first polyacrylic acid cross-linked with pentaerythritol and/or allyl sucrose (e.g., carbomer) and a second polyacrylic acid cross-linked with divinyl glycol (e.g., polycarbophil). In some embodiments, the adhesive matrices may also have a relatively high adhesive strength (e.g., a lap shear adhesive strength of at least about 4 pound force) and/or a relatively high mechanical strength (e.g., burst strength of at least about 100 mmHg gauge).

According to certain but not necessarily all embodiments, it may be advantageous to use a first polyacrylic acid homopolymer cross-linked with pentaerythritol and/or allyl sucrose and a second polyacrylic acid homopolymer cross-linked with divinyl glycol. In some such embodiments, the total amount of the first and second polyacrylic acids within the adhesive matrix can be greater than or equal to about 50%, greater than or equal to about 55%, greater than or equal to about 75%, greater than or equal to about 80%, greater than or equal to about 85%, greater than or equal to about 90%, greater than or equal to about 95%, greater than or equal to about 96%, greater than or equal to about 97%, greater than or equal to about 98%, greater than or equal to about 98.5%, greater than or equal to about 99%, or greater than or equal to about 99.5%.

In some embodiments, the weight percentage of all polyacrylic acids (e.g., polycarbophil and carbomer) in the adhesive matrix and/or composition may be greater than or equal to about 50%, greater than or equal to about 55%, greater than or equal to about 75%, greater than or equal to about 80%, greater than or equal to about 85%, greater than or equal to about 90%, greater than or equal to about 95%, greater than or equal to about 96%, greater than or equal to about 97%, greater than or equal to about 98%, greater than or equal to about 98.5%, greater than or equal to about 99%, or greater than or equal to about 99.5%. In some instances, the weight percentage may be less than or equal to about 100%, less than or equal to about 99.5%, less than or equal to about 99%, less than or equal to about 98.5%, less than or equal to about 98%, less than or equal to about 97%, less than or equal to about 96%, less than or equal to about 95%, less than or equal to about 90%, less than or equal to about 85%, less than or equal to about 80%, less than or equal to about 75%, less than or equal to about 70%, less than or equal to about 65%, or less than or equal to about 60%. Combinations of the above referenced ranges are also possible (e.g., greater than or equal to 50% and less than or equal to about 100%, greater than or equal to 75% and less than or equal to about 100%). One of ordinary skill of the art would be knowledgeable of methods to determine the weight percentage of polyacrylic acid. For example, the weight percentage of polyacrylic acid in an adhesive composition may be determined using high pressure liquid chromatography (HPLC).

In some embodiments, the adhesive matrix may contain a relatively low percentage of liquid. For instance, in some embodiments, the weight percentage of all liquid in the adhesive composition may be less than or equal to about 8 wt. %, less than or equal to about 5 wt. %, less than or equal to about 4 wt. %, less than or equal to about 3 wt. %, less than or equal to about 2 wt. %, less than or equal to about 1 wt. %, less than or equal to about 0.5 wt. %, less than or equal to about 0.1 wt. %, less than or equal to about 0.05 wt. %, less than or equal to about 0.01 wt. %, less than or equal to about 0.005 wt. %, less than or equal to about 0.001 wt. %, or less than or equal to about 0.0005 wt. %. In some instances, the weight percentage may be greater than or equal to about 0.0001 wt. %, greater than or equal to about 0.0005 wt. %, greater than or equal to about 0.001 wt. %, greater than or equal to about 0.005 wt. %, greater than or equal to about 0.01 wt. %, greater than or equal to 0.05 wt. %, greater than or equal to about 0.1 wt. %, greater than or equal to about 0.5 wt. %, greater than or equal to about 1 wt. %, greater than or equal to about 2 wt. %, greater than or equal to about 3 wt. %, or greater than or equal to about 4 wt. %. Combinations of the above referenced ranges are also possible (e.g., greater than or equal to 0.0001 wt. % and less than or equal to about 5 wt. %, greater than or equal to 0.0001 wt. % and less than or equal to about 1 wt. % greater than or equal to 0.0001 wt. % and less than or equal to about 0.1 wt. %). In embodiments in which more than one type of liquid (e.g., ethanol) is present in the adhesive matrix, each type of liquid (e.g., non-aqueous polar solvent, non-aqueous liquid) may independently have a weight percentage with respect to the adhesive matrix in one or more of the ranges described above, provided that, for embodiments in which the total percentage of liquid falls within the above-described ranges, the total percentage is less than or equal to about 8 wt. % (e.g., less than or equal to about 5 wt. %). The weight percentage may be determined as using gas chromatography.

In some embodiments, in the adhesive matrix, the ratio of the total mass of polyacrylic acid(s) (e.g., the first and second polyacrylic acids, and/or other polyacrylic acids) to the total mass of liquid(s) (e.g., the residual non-aqueous liquid and/or non-aqueous polar solvent, and/or other liquids) is from about 10,000:1 to about 19:1. In some embodiments, in the adhesive matrix, the ratio of the total mass of the polyacrylic acid(s) to the total mass of the liquid(s) is equal to or greater than 19:1, equal to or greater than 25:1, equal to or greater than 50:1, equal to or greater than 75:1, equal to or greater than 100:1, equal to or greater than 150:1, equal to or greater than 200:1, equal to or greater than 250:1, equal to or greater than 500:1, equal to or greater than 750:1, equal to or greater than 1,000:1, equal to or greater than 2,500:1, equal to or greater than 5,000:1, or equal to or greater than 7,500:1. In some instances, in the adhesive matrix, the ratio of the total mass of the polyacrylic acid(s) to the total mass of the liquid(s) is less than or equal to about 10,000:1, less than or equal to about 7,500:1, less than or equal to about 5,000:1, less than or equal to about 2,500:1, less than or equal to about 1,000:1, less than or equal to about 750:1, less than or equal to about 500:1, less than or equal to about 250:1, less than or equal to about 150:1, less than or equal to about 100:1, less than or equal to about 75:1, or less than or equal to about 50:1. Combinations of the above referenced ranges are also possible (e.g., greater than or equal to 19:1 and less than or equal to about 10,000:1, greater than or equal to 19:1 and less than or equal to about 1,000:1).

In some embodiments, the adhesive composition and/or matrix may not contain water. In other embodiments, the adhesive composition and/or matrix may contain a relatively low percentage of water. For instance, in some embodiments, the weight percentage of water in the adhesive composition may less than or equal to about 5%, less than or equal to about 3%, less than or equal to about 1%, less than or equal to about 0.5%, less than or equal to about 0.1%, less than or equal to about 0.05%, less than or equal to about 0.01%, less than or equal to about 0.005%, less than or equal to about 0.001%, or less than or equal to about 0.0005%. In some instances, the weight percentage of water in the adhesive composition may be greater than or equal to about 0.0001%, greater than or equal to about 0.0005%, greater than or equal to about 0.001, greater than or equal to about 0.005%, greater than or equal to about 0.01%, greater than or equal to about 0.05%, greater than or equal to about 0.1%, greater than or equal to about 0.5%, or greater than or equal to about 1%. Combinations of the above referenced ranges are also possible (e.g., greater than or equal to 0.0001 wt. % and less than or equal to about 5 wt. %, greater than or equal to 0.0001 wt. % and less than or equal to about 1% greater than or equal to 0.0001 wt. % and less than or equal to about 0.1 wt. %).

In some embodiments, adhesive matrices produced via the inventive methods disclosed may have superior adhesive and mechanical properties to many conventional tissue adhesives formed from similar materials using conventional techniques. For instance, in some embodiments, the adhesive matrix may have a relatively high burst strength. In some embodiments, the adhesive matrix may have a burst strength of greater than or equal to about 100 mmHg (gauge), greater than or equal to about 150 mmHg (gauge), greater than or equal to about 200 mmHg (gauge), greater than or equal to about 250 mmHg (gauge), greater than or equal to about 300 mmHg (gauge), greater than or equal to about 350 mmHg (gauge), greater than or equal to about 400 mmHg (gauge), greater than or equal to about 450 mmHg (gauge), or greater than or equal to about 500 mmHg (gauge). In some instances, the burst strength may be less than or equal to about 600 mmHg (gauge), less than or equal to about 550 mmHg (gauge), less than or equal to about 500 mmHg (gauge), less than or equal to about 450 mmHg (gauge), less than or equal to about 400 mmHg (gauge), less than or equal to about 350 mmHg (gauge), less than or equal to about 300 mmHg (gauge), less than or equal to about 250 mmHg (gauge), or less than or equal to about 200 mmHg (gauge). Combinations of the above-referenced ranges are also possible (e.g., greater than or equal to about 100 mmHg (gauge) and less than or equal to about 600 mmHg (gauge), greater than or equal to about 150 mmHg (gauge) and less than or equal to about 600 mmHg (gauge)). Other values of burst strength are also possible. The burst strength may be determined according to the standard ASTM F2392-04.

In some embodiments, the adhesive matrix may be a self-supporting matrix. A matrix is generally considered to be self-supporting when the matrix does not dissociate into multiple pieces when suspended from one end under the force of gravity. A cohesive film that can be handled without breaking into multiple pieces under the force of gravity is an example of a material that is self-supporting. A layer of particulate powder that cannot be handled without dissociating into individuated particles is an example of a material that is not self-supporting.

According to certain embodiments, the adhesive matrix may be flexible. A flexible material is a material that can be elongated from an un-stressed state such that the length of at least one dimension of the material is increased to at least about 105% of the length of the un-stressed dimension without fracturing. According to certain embodiments, the adhesive matrix can be elongated from an un-stressed state such that the length of at least one dimension of the adhesive matrix is increased to at least about 110%, at least about 125%, at least about 150%, or at least about 200% of the length of the un-stressed dimension without fracturing.

In some embodiments, the adhesive matrix may be elastic. An elastic material is a material that is capable of returning substantially to its original shape spontaneously after distortion (e.g., contraction or dilatation) from its original shape. In certain embodiments, at least one dimension of the adhesive matrix exhibits substantially reversible distortion when the dimension is compressed from its initial (un-stressed) length to a length that is less than about 95% of its initial length (or, in some embodiments, less than about 75%, less than 60%, or less than 50% of its initial length). In some embodiments, at least one dimension of the adhesive matrix exhibits substantially reversible distortion when the dimension is elongated from its initial (un-stressed) length to a length that is at least about 105% of its initial length (or, in some embodiments, at least about 110%, at least about 125%, at least about 150%/o, or at least about 200% of its initial length). An article exhibits "substantially reversible distortion" when, after a dimension of the article has been deformed, the dimension of the article spontaneously returns to a length that is within 10% (or within 5%, or within 2%) of its original length.

In certain embodiments, the adhesive matrix is continuous. In some such cases, the coefficient of variation in the thickness of the adhesive matrix across at least a portion (e.g., across at least 90%, across at least 95%, or across substantially 100%) of its surface is less than or equal to about 20% (e.g., less than or equal to about 20%, less than or equal to about 15%, less than or equal to about 10%, less than or equal to about 5%). In some embodiments, the adhesive matrix is not a powder. According to certain embodiments, less than 10 wt. %, less than 5 wt. %, or less than 1 wt. % of the adhesive matrix is made up of particulate matter having an average largest cross-sectional dimension of less than or equal to about 100 nm.

In certain embodiments, the adhesive matrix may have a lap shear adhesive strength of greater than or equal to about 1.0 pound force. In some embodiments, the adhesive matrix may have a lap shear adhesive strength of greater than or equal to about 1.5 pound force, greater than or equal to about 2 pound force, greater than or equal to about 2.5 pound force, greater than or equal to about 3 pound force, greater than or equal to about 3.5 pound force, greater than or equal to about 4 pound force, greater than or equal to about 4.5 pound force, greater than or equal to about 5 pound force, greater than or equal to about 5.5 pound force, greater than or equal to about 6 pound force, or greater than or equal to about 8 pound force. In some instances, the lap shear adhesive strength may be less than or equal to about 10 pound force, less than or equal to about 8 pound force, less than or equal to about 7.5 pound force, less than or equal to about 7 pound force, less than or equal to about 6.5 pound force, less than or equal to about 6 pound force, less than or equal to about 5.5 pound force, less than or equal to about 5 pound force, less than or equal to about 4.5 pound force, less than or equal to about 4 pound force, less than or equal to about 3.5 pound force, less than or equal to about 3 pound force, or less than or equal to about 2 pound force. Combinations of the above-referenced ranges are also possible (e.g., greater than or equal to about 2 pound force and less than or equal to about 10 pound force, greater than or equal to about 4 pound force and less than or equal to about 10 pound force). Other values of burst strength are also possible. The lap shear adhesive strength may be determined according to the standard ASTM F2255-05 on a glass substrate instead of tissue.

Without being bound by theory, it is believed that the beneficial adhesive and mechanical strength of the adhesive matrix, described herein, is due in part to the interactions between matrix components that are allowed and/or induced to occur during formation of the matrix. It is believed that certain matrix components, such as different polyacrylic acids, may physically entangle or form chemical bonds during certain portions of the method, as described in more detail below. For instance, in some embodiments, one or more matrix components (e.g., polyacrylic acid) may associate with itself or another component via a chemical interaction, such as a non-covalent bond or a covalent bond. In some cases, the bond is a non-covalent bond such as a hydrogen bond, ionic bond, dative bond, and/or a Van der Waals interaction. For example, one or more matrix components may include at least one hydrogen atom capable of interacting with a pair of electrons on a hydrogen-bond acceptor of a binding partner to form the hydrogen bond. In some embodiments, a molecule and/or a binding partner may include an electron-rich or electron-poor moiety, such that it may form an electrostatic interaction with another of a binding partner and/or molecule, respectively. One or more of the matrix components (e.g., polyacrylic acid) may comprise functional groups capable of forming such bonds.

In general, any suitable polyacrylic acid may be used to form the adhesive matrix. In some embodiments, the polyacrylic acid(s) may be selected based on the intended use of the agent. For instance, in some embodiments, the polyacrylic acid(s) may be selected based on its compatibility with pharmaceutical applications and other consumer products (e.g., cosmetics, food).

As used herein, the term "polyacrylic acid" refers to a polymer molecule with or without cross-links comprising at least about 100 optionally substituted acrylic acid and/or acrylate repeat units, wherein the degree of substitution of the acid or acrylate moiety is less than or equal to about 2 (e.g., less than or equal to about 0.8). In certain embodiments, the degree of substitution of the acid or acrylate moiety is less than or equal to about 2, less than or equal to about 1.8, less than or equal to about 1.5, less than or equal to about 1.2, less than or equal to about 1, less than or equal to about 0.8, less than or equal to about 0.6, less than or equal to about 0.5, less than or equal to about 0.4, less than or equal to about 0.3, or less than or equal to about 0.2. In some embodiments, at least a portion of carboxylic acid moieties in the polyacrylic acid may be optionally substituted. In such cases, the degree of substitution of the carboxylic acid moieties in the polyacrylic acid may be as described above. In certain embodiments, at least a portion of the carboxylic acid moieties may be substituted with a cross-linking agent (e.g., allyl sucrose, divinyl glycol, pentaerythritol). In some embodiments, polymer molecules are generally extended molecular structures comprising backbones which optionally contain pendant side groups, wherein the term backbone is given its ordinary meaning as used in the art, e.g., a linear chain of atoms within the polymer molecule by which other chains may be regarded as being pendant. Typically, but not always, the backbone is the longest chain of atoms within the polymer. Polymers may be linear or branched. In some embodiments, the polyacrylic acid(s) may be a co-polymer, for example, a block, alternating, or random co-polymer. In other instances, the polyacrylic acid(s) are homopolymers. In certain embodiments in which the polyacrylic acid is a co-polymer, the mole fraction of acrylic acid and/or acrylate repeat unit in the co-polymer may be greater than or equal to about 0.5, greater than or equal to about 0.6, greater than or equal to about 0.7, greater than or equal to about 0.8, or greater than or equal to about 0.9 and less than or equal to about 1.0 (e.g., less than or equal to about 0.9, less than or equal to about 0.8)

It should be understood that, when determining the mass and/or a weight percentage of one or more "polyacrylic acids" within a particular component (e.g., an adhesive matrix) the weight of the "polyacrylic acid" should include the weight of the entire polymer, including contributions from both the polyacrylic acid backbone any covalently attached moieties. For instance, the mass of covalently cross-linked polyacrylic acid includes the polyacrylic acid and the covalently attached cross-linking agent(s). As another example, the entire mass of a co-polymer comprising polyacrylic acid would be included.

In some embodiments, the polyacrylic acid(s) may be cross-linked, for example through covalent bonds, ionic bonds, hydrophobic bonds, and/or metal binding. In some embodiments, the polyacrylic acid may be covalently cross-linked. In general, any suitable cross-linking method may be used. For instance, charged polyacrylic acid may be ionically cross-linked to form a polymer matrix. Those of ordinary skill in the art would be knowledgeable of suitable cross-linking methods. In certain but not necessarily all embodiments, the polyacrylic acid may include a first polyacrylic acid cross-linked with pentaerythritol (e.g., carbomer) and a second polyacrylic acid cross-linked with divinyl glycol (e.g., polycarbophil).

In some embodiments, the polyacrylic acid(s) may be biodegradable. In other embodiments, the polyacrylic acid(s) may be non-degradable. In embodiments where the adhesive matrices are to be comprised in a composition for administration to a subject, the polyacrylic acid(s) may be non-toxic and bioabsorbable.

Commercially available polyacrylic acids specifically contemplated for use herein include, but are not limited to:

Carbopol® homopolymers which comprise acrylic acid cross-linked with allyl sucrose or allyl pentaerythritol (e.g., Carbopol®71G, 971P NF, 974P NF, 980 NF, 981 NF, 5984 EP, 934 NF, 934P NF, 940 NF, 941 NF);

Carbopol® copolymers which comprise acrylic acid and $C_{10-30}$alkyl acrylate cross-linked with allyl pentaerythritol (e.g., Carbopol® 1342 NF);

Carbopol® interpolymers which comprise acrylic acid and/or $C_{10-30}$alkyl acrylate, and a block co-polymer of polyethylene glycol and a long chain alkyl acid ester, cross-linked with allyl sucrose or allyl pentaerythritol (e.g., Carbopol® ETD2020 NF, Ultrez 10 NF);

a polycarbophil polymer, such as Noveon® AA-1 Polycarbophil, which comprises acrylic acid cross-linked with divinyl glycol;

Pemulen™ polymers which comprise acrylic acid and $C_{10-30}$alkyl acrylate cross-linked with allyl pentaerythritol (e.g., TR-1 NF, TR-2 NF); and Ashland™ carbomers which comprise cross-linked polyacrylic acid (e.g., Ashland™ 940, 941, 980, and 981 carbomers).

In some embodiments, the polyacrylic acid(s) may have a certain average molecular weights (e.g., $M_n$, $M_w$). As known to those of ordinary skill in the art, the number average ($M_n$) and weight average ($M_w$) are defined by the corresponding equations below, where $N_i$ is the number of molecules of each polymer species and $M_i$ is the molar mass of that polymer species.

$$M_n = \frac{\Sigma M_i N_i}{\Sigma N_i}, M_w = \frac{\Sigma M_i^2 N_i}{\Sigma M_i N_i},$$

In some embodiments, the number and/or weight average molecular weight of one or more polyacrylic acid may be greater than or equal to about 400,000 g/mol, greater than or equal to about 500,000 g/mol, greater than or equal to about 750,000 g/mol, greater than or equal to about 1,000,000 g/mol, greater than or equal to about 1,500,000 g/mol, greater than or equal to about 2,000,000 g/mol, greater than or equal to about 3,000,000 g/mol, greater than or equal to about 4,000,000 g/mol, greater than or equal to about 5,000,000 g/mol, greater than or equal to about 6,000,000 g/mol, greater than or equal to about 7,000,000 g/mol, or greater than or equal to about 8,000,000,000 g/mol. In some instances, the number and/or weight average molecular weight of one or more polyacrylic acid may be less than or equal to about 3,000,000,000 g/mol, less than or equal to about 1,000,000,000 g/mol, less than or equal to about 8,000,000 g/mol, less than or equal to about 6,00,000 g/mol, less than or equal to about 5,000,000 g/mol, less than or equal to about 4,000,000 g/mol, less than or equal to about 3,000,000 g/mol, less than or equal to about 2,500,000 g/mol, less than or equal to about 2,000,000 g/mol, less than or equal to about 1,500,000 g/mol, less than or equal to about 1,000,000 g/mol, or less than or equal to about 750,000 g/mol. It should be understood that all combinations of the above-referenced ranges are possible (e.g., greater than or equal to about 400,000 g/mol and less than or equal to about 1,000,000,000 g/mol). Other values of number average molecular weight are possible. The average molecular weights (e.g., $M_n$, $M_w$) described herein were measured using a gel permeation chromatography (GPC).

In some embodiments, the adhesive matrix comprises at least two (or more, e.g., two, three, four, five, six, seven, eight, nine, or ten, or more) different polyacrylic acids which, when mixed together and applied (e.g., to a biological tissue), as described according to certain embodiments herein, lead to an unexpectedly large increase in adhesive and/or mechanical behavior.

In some embodiments, an adhesive matrix may comprise a first polyacrylic acid and second polyacrylic acid. It is generally understood that the first polyacrylic acid and the second polyacrylic acid are different polyacrylic acids, e.g., comprise different components within their structures (e.g., type of cross-linking moiety, degree of cross-linking, chemical structure). In some embodiments, the first polyacrylic acid and the second polyacrylic acid can comprise different components within their respective polymeric backbones. In certain embodiments, the first and second polyacrylic acids comprise one or more different repeat units and/or are each chemically synthesized from different monomers. In some embodiments, the first and second polyacrylic acids do not differ in the backbone structure. In some such embodiments, the first and second polyacrylic acids may differ in the degree of cross-linking, molecular weight, and/or the cross-linking moiety.

Exemplary monomers that the polyacrylic acids, described herein, may be synthesized from include, but are not limited to:

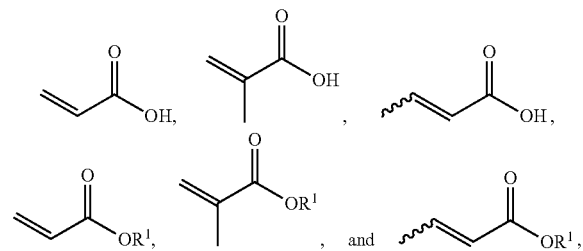

wherein $R^1$ is optionally substituted $C_{1-50}$alkyl, e.g., optionally substituted $C_{10-30}$ alkyl.

In certain embodiments, a polyacrylic acid comprises an acrylic acid monomer:

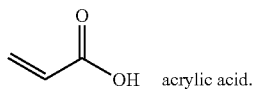

acrylic acid.

In certain embodiments, a polyacrylic acid comprises an acrylic acid monomer and a corresponding ester monomer:

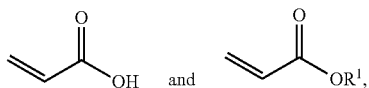

wherein $R^1$ is optionally substituted $C_{1-50}$alkyl, e.g., optionally substituted $C_{10-30}$ alkyl.

In certain embodiments, at least one polyacrylic acid is a polymer of acrylic acid and/or acrylic acid ester cross-linked with divinyl glycol. In certain embodiments, at least one polyacrylic acid is a polymer of acrylic acid and/or acrylic acid ester cross-linked with allyl pentaerythritol. In certain embodiments, at least one polyacrylic acid is a polymer of acrylic acid and/or acrylic acid ester cross-linked with allyl sucrose.

In some embodiments, the first polyacrylic acid is biodegradable. In certain embodiments, the second polyacrylic acid is biodegradable.

In certain embodiments, the first and/or second polyacrylic acids comprise a Carbopol® polymer, e.g., a Carbopol® homopolymer, a Carbopol® copolymer, or a Carbopol® interpolymer. In some embodiments, the first and/or second polyacrylic acids comprise a polycarbophil polymer, e.g. Noveon® AA-1 Polycarbophil. In some embodiments, the first polyacrylic acid comprises a Carbopol® homopolymer, e.g., Carbopol®974P NF, while the second polyacrylic acid comprises a polycarbophil polymer, e.g. Noveon® AA-1 Polycarbophil.

In certain embodiments, the first and/or second polyacrylic acids comprise carbomer homopolymers. In some embodiments, the first and/or second polyacrylic acids comprise polycarbophils. In some embodiments, the first polyacrylic acid comprises a carbomer homopolymer while the second polyacrylic acid comprises a polycarbophil.

In some embodiments in which the adhesive matrix comprises more than one polyacrylic acid, the weight percentage of a single type of polyacrylic acid may be greater than or equal to about 1 wt. %, greater than or equal to about 5 wt. %, greater than or equal to about 10 wt. %, greater than or equal to about 15 wt. %, greater than or equal to about 20 wt. %, greater than or equal to about 25 wt. %, greater than or equal to about 30 wt. %, greater than or equal to about 35 wt. %, greater than or equal to about 40 wt. %, greater than or equal to about 45 wt. %, greater than or equal to about 50 wt. %, greater than or equal to about 55 wt. %, greater than or equal to about 60 wt. %, greater than or equal to about 65 wt. %, greater than or equal to about 70 wt. %, greater than or equal to about 75 wt. %, greater than or equal to about 80 wt. %, greater than or equal to about 85 wt. %, greater than or equal to about 90 wt. %, greater than or equal to about 95 wt. %, or greater than or equal to about 98 wt. %%. In some instances, the weight percentage may be less than or equal to about 100 wt. %, less than or equal to about 95 wt. %, less than or equal to about 90 wt. %, less than or equal to about 85 wt. %, less than or equal to about 80 wt. %, less than or equal to about 75 wt. %, less than or equal to about 70 wt. %, less than or equal to about 65 wt. %, less than or equal to about 60 wt. %, less than or equal to about 55 wt. %, less than or equal to about 50 wt. %, less than or equal to about 45 wt. %, less than or equal to about 40 wt. %, less than or equal to about 35 wt. %, less than or equal to about 30 wt. %, less than or equal to about 25 wt. %, less than or equal to about 20 wt. %, or less than or equal to about 15 wt. %. Combinations of the above referenced ranges are also possible (e.g., greater than or equal to 30 wt. % and less than or equal to about 100 wt. %, greater than or equal to 50 wt. % and less than or equal to about 100 wt. %). The weight percentage may be determined as described above.

The first polyacrylic acid and the second polyacrylic acid may be present in the adhesive matrix and/or composition in any suitable mass ratio. In some embodiments, the mass ratio of the first polyacrylic acid to the second polyacrylic acid within the adhesive matrix and/or composition is from about 1:10 to about 10:1. In some embodiments, the mass ratio of the first polyacrylic acid to the second polyacrylic acid within the adhesive matrix and/or composition is equal to or greater than 1:9, equal to or greater than 1:8, equal to or greater than 1:7, equal to or greater than 1:6, equal to or greater than 1:5, equal to or greater than 1:4, equal to or greater than 1:3, equal to or greater than 1:2, equal to or greater than 1:1.5, or equal to or greater than 1:1.2. In some instances, the mass ratio of the first polyacrylic acid to the second polyacrylic acid within the adhesive matrix and/or composition is equal to or less than 9:1, equal to or less than 8:1, equal to or less than 7:1, equal to or less than 6:1, equal to or less than 5:1, equal to or less than 4:1, equal to or less than 3:1, equal to or less than 2:1, equal to or less than 1.5:1, or equal to or less than 1.2:1. Combinations of the above-referenced ranges are also possible (e.g., equal to or greater than 1:10 and less than 10:1).

As noted above, certain embodiments relate to inventive adhesive compositions. The adhesive compositions can be used, according to certain embodiments, with substrates (e.g., small intestine submucosa, fibrin-containing substrates, or other substrates), for example, to form tissue patches. It should be understood that the use of the adhesive compositions described herein is not limited to tissue patches, and the adhesives may have other uses.

Figure 2A:
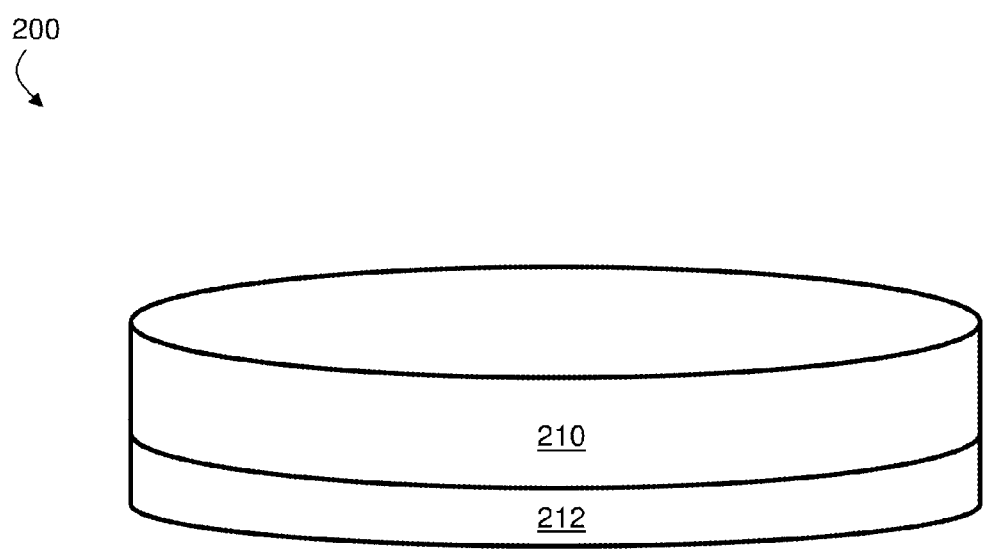
FIG. 2A is a schematic of an adhesive composition, according to certain embodiments.

FIG. 2A is a perspective-view schematic illustration of exemplary article 200 comprising substrate 210 and an adhesive matrix 212 associated with substrate 210. Substrate 210 can, in some cases, correspond to substrate 125 in FIGS. 1A-1C, or it may correspond to another substrate. Adhesive matrix 212 can, in some cases, correspond to adhesive matrix 135 in FIG. 1C, or it may correspond to another adhesive matrix. In certain embodiments, the substrate and adhesive matrix can be configured to be applied to tissue such that the adhesive matrix contacts the tissue. In some embodiments, adhesive matrix 212 is substantially free of loose powder (i.e., it contains loose powder in an amount of less than about 0.1 wt. %, less than about 0.01 wt. %, less than about 0.001 wt. %, or it contains no loose powder).

In certain embodiments, the adhesive matrix can help to achieve immobilization of the overlying substrate on a surface, such as a tissue surface. For example, in some embodiments, adhesive matrix 212 can be configured to enhance the degree to which substrate 210 is immobilized on a tissue surface onto which substrate 210 and adhesive matrix 212 have been applied. In some instances, immobilization of the substrate can be achieved without the need to apply much or any external pressure. In certain embodiments, immobilization of the substrate can be achieved in fewer than 5 minutes, fewer than 120 seconds, fewer than 60 seconds, or fewer than 30 seconds. In certain embodiments, once the substrate has been immobilized, it may remain in place for at least 12 hours, at least 24 hours, at least 48 hours, or at least 72 hours (and/or, in some embodiments, up to 30 days, up to 120 days, and/or until the substrate biodegrades).

In certain embodiments, the adhesive can be selected or configured such that it does not form covalent chemical bonds with the underlying surface to which it is applied (e.g., an underlying tissue surface). In certain embodiments, the adhesive matrix can be selected or configured to interact with the surface to which it is applied (e.g., a tissue surface) via hydrogen bonding and/or van der Waals forces. In some embodiments the adhesive matrix can be configured to interact with the underlying surface (e.g., tissue surface) via physisorption (sometimes also referred to as adhesive dispersion). Such adhesives can be advantageous, for example, when used to adhere tissue, at least in part because, while they effectively immobilize the patch on the tissue, they do not form strong (or permanent) bonds, which can lead to tissue damage. Of course, while non-covalently bound adhesive matrices have been described, it should be understood that the invention is not limited to the use of such adhesives, and in other cases, adhesives that covalently bond to underlying surfaces (e.g., tissue surfaces) can be employed.

In some embodiments, the substrate can be applied to a tissue surface and can be allowed to integrate with the underlying tissue.

The adhesive matrix can be applied to or otherwise associated with the substrate via the methods, described herein. In other embodiments, the adhesive matrix can be formed on another substrate, removed from the substrate on which it is formed, and subsequently applied to a different substrate, prior to applying the adhesive matrix to tissue.

Figure 2B:
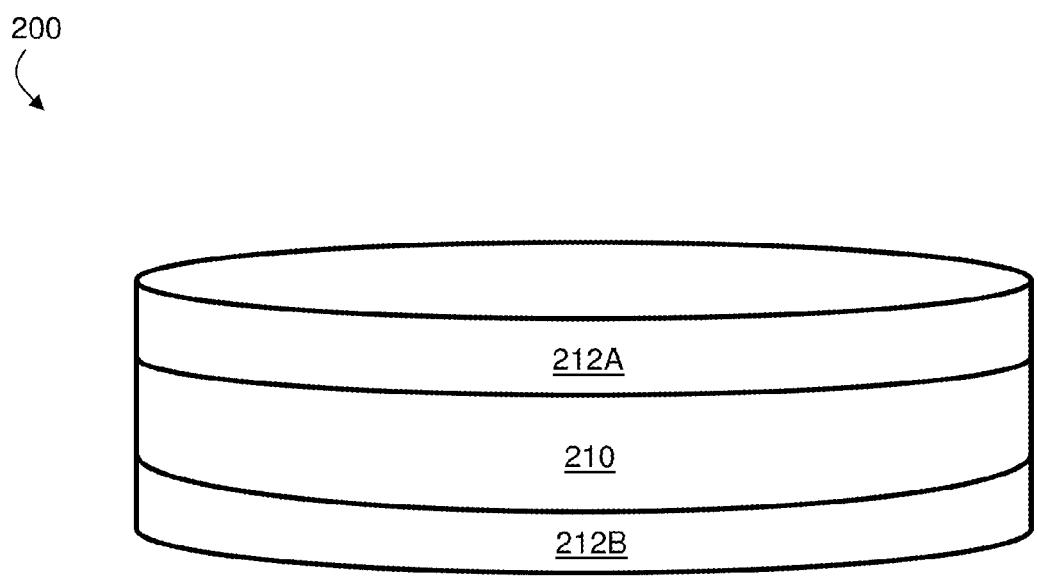
FIG. 2B is a schematic of an adhesive composition, according to certain embodiments.

While FIG. 2A illustrates an embodiment in which an adhesive matrix is applied to one side of a substrate, in certain embodiments, adhesive matrix can be applied to multiple sides of the substrate. For example, in FIG. 2B, adhesive matrix 212A and 212B are arranged on opposite sides of substrate 210. When arranged in this fashion, the substrate and adhesive can be used to join two surfaces, with a first surface adhering to adhesive matrix 212A and a second surface adhering to adhesive matrix 212B. For example, substrates with adhesive applied on both sides can be used to join two surfaces of skin, a pleural space, spaces between bone tissue surfaces, and other such cavities within a body.

In certain cases, and as described in more detail below, the substrate can comprise fibrin, tissue (e.g., small intestine submucosa), synthetic polymers, cellulose, diaphragm, porcine skin, bovine skin, human skin, pericardium, extracellular matrix collagen, or amnion. In some such embodiments, the adhesive matrix is configured to immobilize the substrate (e.g., by anchoring the substrate to the tissue to which it is applied) and provide support while fibrinogen and/or fibrin from the tissue integrates with the fibrin and/or fibrinogen within the substrate. For example, fibrinogen and/or fibrin within the tissue can migrate from the tissue, through the adhesive, and into the substrate, where the fibrinogen and/or fibrin from the tissue can polymerize and/or cross-link with fibrinogen and/or fibrin within the substrate. The integration of the fibrin and/or fibrinogen within a subject's tissue with the fibrin and/or fibrinogen within the substrate can lead to the formation of a more robust interface and/or integration region between the tissue, the adhesive, and the substrate, which can produce enhanced tissue repair.

Certain embodiments employ substrates (including fibrin-containing substrates and other substrates) having low liquid (e.g., low water) content. For example, in some embodiments, the substrate has a liquid content of less than about 20 wt. %, less than about 15 wt. %, less than about 12 wt. %, or less than about 10 wt. %. In some embodiments, the substrate has a water content of less than about 20 wt. %, less than about 15 wt. %, less than about 12 wt. %, or less than about 10 wt. %. Such substrates may, according to certain embodiments, have any of the fibrin contents and/or compositional properties described elsewhere herein.

While the present invention is not limited to the use of substrates made of any particular materials, certain embodiments relate to fibrin-containing substrates. In some embodiments, the substrate has a combined fibrin and fibrinogen content of at least about 50 wt. %, at least about 75 wt. %, at least about 80 wt. %, at least about 85 wt. %, or at least about 90 wt. %. In some embodiments, the substrate has a fibrin content of at least about 50 wt. %, at least about 75 wt. %, at least about 80 wt. %, at least about 85 wt. %, or at least about 90 wt. %.

Fibrin-containing substrates with low amounts of water can be fabricated, for example, by exposing a solid matrix comprising water and fibrin to a dehydrating agent (e.g., a dehydrating liquid) such that water is displaced or otherwise removed from the solid matrix. In some such embodiments, at least a portion (or all) of the water within the solid matrix can be displaced and/or otherwise removed by the dehydrating agent, resulting in a substrate with a relatively low water content. A variety of dehydrating agents can be used in association with such methods. Examples of liquid dehydrating agents that can be used include, but are not limited to, non-polar liquids (e.g., pentane, cyclopentane, hexane, cyclohexane, benzene, 1,4-Dioxane, chloroform, and diethyl ether); polar aprotic liquids (e.g., dichloromethane (DCM), tetrahydrofuran (THF), ethyl acetate, acetone, dimethylformamide (DMF), acetonitrile, dimethyl sulfoxide (DMSO), and propylene carbonate); polar protic liquids (e.g., formic acid, butanol, isopropanol, propanol, ethanol, methanol, acetic acid, and nitromethane). and/or others (e.g., butylacetate, chlorobenzene, diethylether, diisoproylether, ethylmethylketone, heptane, isoamylalcohol, pentachloroethane, tetracholoethane, tetrachloromethane, toluene, and xylene).

Fibrin-containing substrates (e.g., patches) can be manufactured using a variety of suitable methods. In some embodiments, fibrin-containing substrates (e.g., patches) are made by applying a compressive force to a liquid-containing composition comprising fibrinogen (and/or fibrin) between two surfaces (e.g., within a syringe or other chamber). A filter can be placed within or near the volume in which the compressive force is applied to the liquid-containing composition such that unwanted material (e.g., some liquid components (e.g., water), blood cells, etc.) is passed through the filter while desirable components (e.g., fibrin and/or fibrinogen) are retained by the filter to form the fibrin-containing substrate. In this way, the concentration of fibrin (and/or fibrinogen) can be increased, potentially substantially, as the compressive force is applied to the liquid-containing composition. In addition, in some embodiments, at least a portion of the fibrinogen and/or fibrin can chemically react (e.g., the fibrinogen can polymerize to form fibrin and/or the fibrin can cross-link) before, during, and/or after application of the compressive force. Reaction and concentration via application of the compressive force (e.g., by removing at least a portion of the non-fibrin and/or non-fibrinogen components, such as liquid components (e.g., water), blood cells, and the like) can lead to the formation of a highly-concentrated, mechanically robust substrate (e.g., patch) that can be handled relatively easily and provide good structural reinforcement at a wet site, such as a bleeding wound. In certain embodiments, additional advantage, economy, convenience, and/or safety is gained by the use of autologous whole blood as the liquid-containing composition to which a compressive force is applied to form the substrate (e.g., patch). Examples of such methods are described, for example, in International Patent Application Publication No. WO 2013/116633, filed Feb. 1, 2013, published on Aug. 8, 2013, and entitled "Tissue Patches and Associated Systems, Kits, and Methods"; U.S. Patent Publication No. US 2013/0202656, filed Oct. 4, 2012, published on Aug. 8, 2013, and entitled "Systems and Kits for the Fabrication of Tissue Patches"; U.S. Patent Publication No. US 2013/0202674, filed on Oct. 4, 2012, published on Aug. 8, 2013, and entitled "Tissue Patch"; and U.S. Patent Publication No. US 2013/0202675, filed Oct. 4, 2012, published on Aug. 8, 2013, and entitled "Systems and Methods for the Fabrication of Tissue Patches," each of which is incorporated herein by reference in its entirety for all purposes.

In some embodiments, the substrate can contain relatively highly cross-linked fibrin. Highly cross-linked fibrin can be achieved, for example, by including a cross-linking agent (e.g., thrombin, Factor XIII, and/or calcium-containing compounds, and the like) during the formation of the substrate. One of ordinary skill in the art would be capable of determining the amount of cross-linking in a given fibrin-containing medium by using one exemplary screening test in which the fibrin-containing medium is submerged in an aqueous solution of 8 molar (i.e., 8M) urea and maintained at a temperature of 25° C. Under such conditions, samples containing highly cross-linked fibrin can take a relatively long time to dissolve, while samples containing slightly cross-linked fibrin (or fibrin that is not cross-linked at all) can be dissolved relatively quickly. In certain embodiments, upon submerging the fibrin-containing substrate in an 8M aqueous solution of urea at 25° C., the fibrin-containing portion will retain its structural integrity (i.e., less than 50 wt. % of the portion will dissociate) over a period of at least about 2 hours, at least about 8 hours, at least about 24 hours, at least about 48 hours, at least about 72 hours, at least about 1 week, or at least about 1 month (and/or, up to about 1 year, or longer). In certain embodiments, upon submerging the fibrin-containing substrate in a 6M aqueous solution of urea at 25° C., the fibrin-containing portion will retain its structural integrity (i.e., less than 50 wt. % of the portion will dissociate) over a period of at least about 2 hours, at least about 8 hours, at least about 24 hours, at least about 48 hours, at least about 72 hours, at least about 1 week, or at least about 1 month (and/or, up to about 1 year, or longer). Of course, the fibrin-containing substrate described herein can also be designed to include fibrin that is cross-linked to a less substantial degree, and in some cases, to include fibrin that is not cross-linked. In certain embodiments, the conditions under which the substrate is formed can be selected such that the final substrate includes the desired degree of cross-linking, for example, by adding an appropriate amount of cross-linking agent to the liquid medium to which a compressive force is to be applied.

In certain embodiments, the substrates (e.g., fibrin-containing substrates) can have relatively high tensile strengths. In some embodiments, the substrate has a tensile strength of at least about 175 kPa, at least about 250 kPa, at least about 500 kPa, at least about 600 kPa, or between about 175 kPa and about 650 kPa, when measured as a true stress at break.

In certain embodiments, the substrate component (e.g., a fibrin-containing substrate component) can maintain its strength and/or flexibility after sterilization. For example, in some embodiments, the substrate component has a Young's modulus of about 10 GPa or less, of about 1 GPa or less, or of about 100 kPa or less after sterilization using gamma radiation at an intensity of 30 kGy. In some embodiments, the substrate material has a Young's modulus of from about 1 kPa to about 10 GPa, of from about 1 kPa to about 1 GPa, or of from about 1 kPa to about 100 kPa after sterilization using gamma radiation at an intensity of 30 kGy.

In certain embodiments, the substrate (e.g., substrate 210 in FIG. 2A) is biodegradable. In certain embodiments, the biodegradable materials described herein (e.g., in the substrate and/or in the adhesive) can be broken down such that less than 2 wt. %, less than 1 wt. %, less than 0.1 wt. %, or less than 0.01 wt. % of their mass remains in a subject (e.g., a human subject) after fewer than 365 days, fewer than 180 days, fewer than 90 days, fewer than 60 days, or fewer than 30 days of being located within the subject.

In certain embodiments, the substrate is substantially free of thrombin. An article (e.g., a substrate such as a fibrin-containing substrate, a patch, an adhesive material, etc.) is said to be "substantially free of thrombin" when the article contains thrombin in an amount of less than or equal to 0.0025 wt. %. In some embodiments, an article that is substantially free of thrombin contains thrombin in an amount of less than or equal to 0.001 wt. %, less than or equal to 0.00025 wt. %, or less than or equal to 0.0001 wt. %. In some embodiments, an article that is substantially free of thrombin is completely free of thrombin. In some embodiments, an article that is substantially free of thrombin is also substantially free of prothrombin (i.e., it contains prothrombin in an amount of less than or equal to 0.0025 wt. %). In some embodiments, an article that is substantially free of thrombin and/or prothrombin contains prothrombin in an amount of less than or equal to 0.001 wt. %, less than or equal to 0.00025 wt. %, or less than or equal to 0.0001 wt. %. In some embodiments, an article that is substantially free of thrombin and/or prothrombin is completely free of prothrombin. However, the invention is not strictly limited to thrombin-free applications, and in other embodiments, thrombin can be mixed in with and/or coated on the adhesive matrices.

As illustrated in FIG. 2A, substrate 210 (which can be, for example, a solid matrix) is in the form of a cylindrical disc with a substantially circular cross-sectional geometry. In other embodiments, the substrate (or the entire article, including both substrate and adhesive matrix) can have other cross-sectional geometries such as, for example, substantially elliptical, polygonal (e.g., including any number of sides such as in the form of a triangle, a quadrilateral (e.g., rectangular or substantially square), etc.), irregularly-shaped, or any other suitable shape.

In some embodiments, the substrate (e.g., substrate 210), adhesive matrix (212) and/or article (e.g., article 200) can be in the form of a sheet or film. For example, the substrate and/or article may have an aspect ratio (measured as the ratio of the maximum cross-sectional dimension to the minimum thickness of the substrate or article, for example, upon inspection) of at least about 5:1, at least about 10:1, between about 5:1 and about 100:1, or between about 5:1 and about 50:1. In certain embodiments, the substrate and/or article has an average thickness of between about 500 microns and about 1 cm. The average thickness of a component can be determined by measuring the thickness of the component at a representative number of locations and number averaging the results. In certain embodiments, the substrate and/or article has at least one cross-sectional dimension of at least about 1 cm, at least about 10 cm, at least about 50 cm, or greater. As one particular example, the substrate comprises a disc (e.g., a substantially cylindrical disc) with a thickness of between about 500 microns and about 1 cm, and a maximum cross-sectional diameter orthogonal to the thickness that is at least about 1 cm, at least about 10 cm, at least about 50 cm, or greater.

The adhesive matrix and the substrate can be in contact, either directly (i.e., in direct contact) or indirectly (i.e., in indirect contact), in certain embodiments. For example, as illustrated in FIG. 2A, substrate 210 and adhesive matrix 212 are in direct contact. However, in other embodiments, one or more solid intermediate materials can be positioned between the substrate and the adhesive matrix such that the substrate and the adhesive matrix do not contact each other directly, in which case, the substrate and the adhesive matrix would be said to be in indirect contact. Both articles in direct contact with each other and articles in indirect contact with each other are considered to be in contact with each other, as described herein.

In certain embodiments, adhesive matrix 212 comprises a water activated polyacrylic acid polymeric adhesive. Those of ordinary skill in the art are familiar with water-activated polyacrylic acid polymeric adhesives, which are adhesive polyacrylic acids that are rendered tacky by application of water. One can use a water-activated polymeric adhesive by applying water just prior to use, or by relying on water at the application site, to render the adhesive tacky.

Any suitable water-activated polymeric adhesive can be used. In some embodiments, the water-activated polymeric adhesive comprises any of the adhesive compositions described above that would be activated upon the application of water.

In general, the adhesive matrix may have any suitable shape or dimension. In some embodiments, the dimensions of the adhesive matrix may be selected as desired. It should be understood that the adhesive matrix can have any suitable cross-sectional dimension. For instance, in some embodiments, adhesive matrix may have a maximum cross-sectional dimension of greater than or equal to about 0.01 cm, greater than or equal to about 0.05 cm, greater than or equal to about 0.1 cm, greater than or equal to about 1 cm, greater than or equal to about 2 cm, greater than or equal to about 5 cm, greater than or equal to about 10 cm, greater than or equal to about 20 cm, greater than or equal to about 30 cm, greater than or equal to about 40 cm, greater than or equal to about 50 cm, greater than or equal to about 60 cm, greater than or equal to about 70 cm, greater than or equal to about 80 cm, or greater than or equal to about 90 cm. In some instances, an adhesive matrix, may have a maximum cross-sectional dimension of less than or equal to about 100 cm, less than or equal to about 90 cm, less than or equal to about 80 cm, less than or equal to about 70 cm, less than or equal to about 60 cm, less than or equal to about 50 cm, less than or equal to about 40 cm, less than or equal to about 30 cm, less than or equal to about 20 cm, less than or equal to about 10 cm, or less than or equal to about 5 cm. Combinations of the above-referenced ranges are also possible (e.g., greater than or equal to about 1 cm and less than or equal to about 100 cm). Other values of maximum cross-sectional dimensions are also possible.

In some cases, at least one or at least two cross-sectional dimensions (e.g., a length and a width) of the adhesive matrix may be greater than or equal to about 0.01 cm, greater than or equal to about 0.05 cm, greater than or equal to about 0.1 cm, greater than or equal to about 1 cm, greater than or equal to about 2 cm, greater than or equal to about 5 cm, greater than or equal to about 10 cm, greater than or equal to about 20 cm, greater than or equal to about 30 cm, greater than or equal to about 40 cm, greater than or equal to about 50 cm, greater than or equal to about 60 cm, greater than or equal to about 70 cm, greater than or equal to about 80 cm, or greater than or equal to about 90 cm. In some instances, at least one or at least two cross-sectional dimensions of adhesive matrix may be less than or equal to about 100 cm, less than or equal to about 90 cm, less than or equal to about 80 cm, less than or equal to about 70 cm, less than or equal to about 60 cm, less than or equal to about 50 cm, less than or equal to about 40 cm, less than or equal to about 30 cm, less than or equal to about 20 cm, less than or equal to about 10 cm, or less than or equal to about 5 cm. Combinations of the above-referenced ranges are also possible (e.g., greater than or equal to about 1 cm and less than or equal to about 100 cm). Other values are also possible.

In some embodiments, the adhesive matrix may be relatively thin. In some embodiments, the thickness of the adhesive matrix may be less than or equal to about 1 mm, less than or equal to about 0.9 mm, less than about 0.8 mm, less than or equal to about 0.7 mm, less than or equal to about 0.6 mm, less than or equal to about 0.5 mm, less than or equal to about 0.4 mm, less than or equal to about 0.3 mm, less than or equal to about 0.2 mm, less than or equal to about 0.1 mm, less than or equal to about 0.09 mm, or less than or equal to about 0.08 mm. In some instances, the thickness of the adhesive matrix may be greater than or equal to about 0.03 mm, greater than or equal to about 0.04 mm, greater than or equal to about 0.05 mm, greater than or equal to about 0.06 mm, greater than or equal to about 0.07 mm, greater than or equal to about 0.08 mm, greater than or equal to about 0.09 mm, greater than or equal to about 0.1 mm, greater than or equal to about 0.2 mm, greater than or equal to about 0.3 mm, greater than or equal to about 0.4 mm, greater than or equal to about 0.5 mm, or greater than equal to 0.6 mm. Combinations of the above-referenced ranges are possible (e.g., greater than or equal to about 0.03 mm and less than or equal to about 1 mm, greater than or equal to about 0.5 mm and less than or equal to about 1 mm). Other values of thickness of the adhesive matrix are possible. The thickness may be measured using a micrometer. One of ordinary skill in the art would be knowledge of thickness measurements.

The amount of the adhesive matrix that is formed over the substrate can fall within a number of ranges. In some embodiments, the mass of the adhesive matrix on the substrate is greater than or equal to about 2 mg/cm$^2$, greater than or equal to about 3 mg/cm$^2$, greater than or equal to about 4 mg/cm$^2$, greater than or equal to about 5 mg/cm$^2$, greater than or equal to about 6 mg/cm$^2$, greater than or equal to about 7.5 mg/cm$^2$, greater than or equal to about 10 mg/cm$^2$, greater than or equal to about 12 mg/cm$^2$, or greater than or equal to about 14 mg/cm$^2$. In some embodiments, the mass of the adhesive matrix on the substrate is less than or equal to about 35 mg/cm$^2$, less than or equal to about 30 mg/cm$^2$, less than or equal to about 25 mg/cm$^2$, less than or equal to about 20 mg/cm$^2$, less than or equal to about 18 mg/cm$^2$, or less than or equal to about 16 mg/cm$^2$. Combinations of the above-referenced ranges are also possible (e.g., from about 2 mg/cm$^2$ to about 35 g/cm$^2$, from about 14 mg/cm$^2$ to about 16 mg/cm$^2$). Other ranges are also possible.

In some embodiments, a pharmaceutically active composition, growth factor, or other bioactive composition can be applied to a surface of and/or included within the bulk of one or more regions of any of the articles described herein (e.g., substrate 210 and/or adhesive matrix(s) 212 in FIG. 2A). In certain embodiments, one or more pharmaceutically active compositions can be included within and/or on a surface of the articles (e.g., adhesive matrices, substrates) described herein. In some such embodiments, the article can act as a delivery mechanism for the pharmaceutically active composition. Exemplary pharmaceutically active compositions that be used in association with the articles described herein include, but are not limited to, analgesics, antimicrobial agents (e.g., antibiotics, antifungal, and/or antiviral agents), hormones, insulin, vitamins, and the like. In certain embodiments, the pharmaceutically active composition comprises a small molecule (i.e., a molecule with a molecular weight of less than about 2000 g/mole and, in some instances, less than about 1000 g/mole or less than about 500 g/mole). Exemplary small molecules include, for example, nucleic acids, peptides, polypeptides, peptide nucleic acids, peptidomimetics, carbohydrates, lipids or other organic (carbon containing) or inorganic molecules. In certain embodiments, the pharmaceutically active composition is selected from "Approved Drug Products with Therapeutic Equivalence and Evaluations," published by the United States Food and Drug Administration (F.D.A.) (the "Orange Book").

In certain embodiments, an antimicrobial agent can be applied to a surface of and/or included within the bulk of one or more regions of any of the articles described herein (e.g., substrate 210 and/or adhesive matrix 212 in FIG. 2A). The use of antimicrobial agents or other drugs can be advantageous for a variety of reasons. For example, a growing concern with the use of certain tissue sealants is that the tissue sealant can capture or contain bacteria within or under the surface of the tissue sealant and create an environment in which bacteria can grow. Including an antimicrobial agent within one or more surfaces or volumes of the article can help to combat the growth of bacteria on or around the site to which the article is applied.

A variety of antimicrobial agents can be incorporated into any of the articles described herein (e.g., substrate 210 and/or adhesive matrix(s) 212 in FIG. 2A). The antimicrobial agent may be bacteriocidal, veridical, fungicidal, and/or any combination thereof. In certain embodiments, a zinc-containing material such as a zinc oxide can be used as an antimicrobial agent. Examples of suitable antimicrobial agents that can be used include, but are not limited to, metal-containing compounds (e.g., zinc-containing compounds, silver-containing compounds (e.g., silver nitrate, silver sulfadiazine, silver foams, flammacerium, Acticoat 7, Aquacel-Ag, Silvercel, and/or silver amniotic membrane), gold-containing compounds, copper-containing compounds, tin-containing compounds, chromium-containing compounds, and the like), organic antimicrobial compounds (e.g., organic antibiotics such as tetracycline antibiotics, rifampin, minocycline, and the like), antimicrobial peptide(s) (e.g., defnsins, histone H1.2, cecropin B, recombinant bactericidal/permeability-increasing protein (rBPI), and/or ceragenins), chitosan, topical antibiotics (e.g., mafenide acetate, bacitracin, mupirocin, Neosporin®, polymyxin B, nitrofurazone, and/or nystatin), iodine-based compounds (e.g., povidone-iodine, cadexomer iodine, liposomal iodine, and/or Repithel®, and/or Iocidem™), and the like. Other agents that can be added to the tissue patches described herein include chlorhexidine, superoxidized water, acidified nitrite, p38MAPK inhibitor, probiotic *Lactobacillus*, honey, essential oils, and/or *papaya*.

In some embodiments, one or more growth factors can be included in and/or on a surface of any of the articles described herein (e.g., substrate 210 and/or adhesive matrix(s) 212 in FIG. 2A). Such growth factors can contribute to hemostasis, tissue healing, or other biological processes. For example, in certain embodiments, Platelet Derived Growth Factor (PDGF) can be included within and/or on a surface of an article (e.g., in or on substrate 210 and/or in or on adhesive matrix(s) 212 in FIG. 2A), which can assist in wound healing. Other examples of growth factors that be included include, but are not limited to, growth factors from one or more of the following families: adrenomedullin (AM), angiopoietin (Ang), autocrine motility factor, bone morphogenetic proteins (BMPs), brain-derived neurotrophic factor (BDNF), epidermal growth factor (EGF), erythropoietin (EPO), fibroblast growth factor (FGF), glial cell line-derived neurotrophic factor (GDNF), granulocyte colony-stimulating factor (G-CSF), granulocyte macrophage colony-stimulating factor (GM-CSF), growth differentiation factor-9 (GDF9), hepatocyte growth factor (HGF), hepatoma-derived growth factor (HDGF), insulin-like growth factor (IGF), migration-stimulating factor, myostatin (GDF-8), nerve growth factor (NGF) and other neurotrophins, thrombopoietin (TPO), transforming growth factor alpha (TGF-α), transforming growth factor beta (TGF-β), tumor necrosis factor-alpha(TNF-α), vascular endothelial growth factor (VEGF), placental growth factor (PlGF), and the like.

In certain embodiments, a backing layer can be applied to any of the articles described herein (e.g., substrate 210 and/or adhesive matrix(s) 212 in FIG. 2A). However, it should be understood that backing layers are not required, and in some but not necessarily all embodiments can be advantageous to omit.

As noted elsewhere, certain of the articles described herein (e.g., adhesive matrices) can be used as tissue patches. In certain embodiments, a tissue patch can be assembled and/or used as follows. A substrate can be formed and an adhesive matrix can be placed on the substrate. In some embodiments, the assembled patch can be applied to a tissue surface (e.g., such that the adhesive matrix contacts the tissue surface).

Once applied to a tissue site, blood from the subject can naturally start the coagulation process. In some embodiments, the adhesive matrix can provide an adhesive anchor material that holds the patch in place over the tissue, even when it is bleeding.

Any of the articles described herein (e.g., a substrate, adhesive matrix(s), and/or combinations of substrates and adhesives matrix) can be packaged, according to certain embodiments. For example, in some embodiments, a substrate and/or adhesive(s) may be packaged within a foil pouch or other suitable container. In some embodiments, the container within which the article is packaged is sealed. Packaging the products described herein can allow one to store them for future use. The adhesive composition can be used to produce a patch that is subsequently sterilized and packaged (and optionally stored for days, weeks, months, or longer) for application to a subject at a location remote from the patch production location.

In certain embodiments, the article within the package is sterile (e.g., by sterilizing the article prior to packaging the article).

In certain embodiments, the articles described herein can have a relatively long shelf life. In some embodiments, the adhesives described herein can be packaged and stored at room temperature for a period of at least 1 month, at least 6 months, or at least 1 year without losing a substantial amount (i.e., 5%) of its adhesive properties. In addition, the components used to make certain of the articles described herein (e.g., substrates, adhesives, and/or patches) can have a relatively long shelf life, especially when enclosed in a sterile package.

The articles (e.g., adhesives, substrates, combinations of the two, etc.) described herein can be used in a wide variety of applications including, for example, general surgery, vascular surgery, spine surgery and ophthalmologic surgery. The articles can be configured to be applied to any type of tissue including soft tissue, bone tissue, or any other type of tissue. The articles can be employed to: assist hemostasis in a bleeding area, reduce blood flow from solid organs, assist in sealing suture holes, assist in sealing anastomosis or leaks from hollow organs, assist or replace sutures in surgical procedures (particularly where suturing is difficult or impossible), produce a water-tight closure across portions of tissue (e.g., across a suture line), reinforce tissue (e.g., in reinforcing suture lines including high stress suture lines), perform of tissue approximation, replace sutures, fill dead space or other voids in tissue, and/or in vascular repair (e.g., to seal a vascular defect). In certain embodiments, certain of the articles described herein can be employed to perform gastrointestinal suture line reinforcement, in preventing the formation of seroma (e.g., after surgical procedures), for use as soft tissue (e.g., after breast cancer or other surgical procedures in which tissue may be removed), as burn dressings, and/or for combined hemostasis/sealing and drug delivery.

In some embodiments, certain of the articles described herein (e.g., adhesives, substrates, combinations of the two, etc.) can be used to treat spleen tissue, for example, to inhibit or stop bleeding or the leaking of other bodily fluids and/or to partially or completely fill void(s) in the spleen. In certain embodiments, certain of the articles described herein can be used to treat lung tissue, for example, to inhibit, or stop bleeding or the leaking of other bodily fluids, to partially or completely fill void(s) in the lung, and/or to inhibit or stop the leaking of air from the internal cavity of a lung. In some embodiments, certain of the articles described herein can be used to treat the liver, for example, to inhibit or stop bleeding or the leaking of other bodily fluids from the liver and/or to partially or completely fill void(s) in the liver. In certain embodiments, certain of the articles described herein can be used to treat heart tissue, for example, to inhibit or stop bleeding or the leaking of other bodily fluids, to partially or completely fill void(s) in the heart or associated blood vessels, and/or to inhibit or stop the leaking of blood from an internal cavity of a heart. Certain of the articles described herein can also be used to treat tissues in or near the gastrointestinal tract, for example, to inhibit, or stop bleeding or the leaking of other bodily fluids, to partially or completely fill void(s) in gastrointestinal tissues.

The articles described herein can have a variety of advantageous properties, in certain although not necessarily all embodiments. For example, certain embodiments of the fibrin-containing substrates described herein can be formed and applied at the site of application. Also, as noted above, articles formed according to certain embodiments of the methods described herein can have relatively high tensile strengths. Moreover, some embodiments of the articles described herein are capable of adhering to a wet (e.g., bleeding) tissue surface.

Certain of the substrates, adhesives, and tissue patches described herein can be biocompatible and/or biodegradable. In addition, the substrates, adhesives, and/or tissue patches can be configured such that they do not interfere with any metabolic pathways that would produce significant biologic dysfunction. The use of sterile materials and components to form certain embodiments of the articles described herein can reduce or eliminate the risk of bacterial, viral, or other infectious agents being transmitted as the result of the use of the article.

The articles described herein (e.g., substrates, adhesives, tissue patches, etc.) can be used to treat human subjects, in certain embodiments. In other embodiments, the articles described herein can be used to treat non-human animal subjects. For example, in certain cases, the articles described herein can be used in veterinary applications, for example, those involving horses, dogs, cats, and the like.

The following patent publications are incorporated herein by reference in their entirety for all purposes: International Patent Application Serial No. PCT/US2013/024322 filed Feb. 1, 2013, published as International Patent Publication No. WO 2013/116633 on Aug. 8, 2013, and entitled "Tissue Patches and Associated Systems, Kits, and Methods"; U.S. patent application Ser. No. 13/644,868 filed Oct. 4, 2012, published as U.S. Patent Publication No. US 2013/0202656 on Aug. 8, 2013, and entitled "Systems and Kits for the Fabrication of Tissue Patches"; U.S. patent application Ser. No. 13/644,889 filed Oct. 4, 2012, published as U.S. Patent Publication No. US 2013/0202674 on Aug. 8, 2013, and entitled "Tissue Patch"; and U.S. patent application Ser. No. 13/644,907 filed Oct. 4, 2012, published as U.S. Patent Publication No. US 2013/0202675 on Aug. 8, 2013, and entitled "Systems and Methods for the Fabrication of Tissue Patches." U.S. patent application Ser. No. 14/821,625, filed Aug. 7, 2015, and entitled "Adhesive Compositions and Related Methods," is incorporated herein by reference in its entirety for all purposes.

DEFINITIONS

Chemical Definitions

Definitions of specific functional groups and chemical terms are described in more detail below. The chemical elements are identified in accordance with the Periodic Table of the Elements, CAS version, Handbook of Chemistry and Physics, 75$^{th}$ Ed., inside cover, and specific functional groups are generally defined as described therein. Additionally, general principles of organic chemistry, as well as specific functional moieties and reactivity, are described in *Organic Chemistry*, Thomas Sorrell, University Science Books, Sausalito, 1999; Smith and March *March's Advanced Organic Chemistry*, 5$^{th}$ Edition, John Wiley & Sons, Inc., New York, 2001; Larock, *Comprehensive Organic Transformations*, VCH Publishers, Inc., New York, 1989; and Carruthers, *Some Modern Methods of Organic Synthesis*, 3$^{rd}$ Edition, Cambridge University Press, Cambridge, 1987.

When a range of values is listed, it is intended to encompass each value and sub-range within the range. For example "$C_{1-6}$ alkyl" is intended to encompass, $C_1$, $C_2$, $C_3$, $C_4$, $C_5$, $C_6$, $C_{1-6}$, $C_{1-5}$, $C_{1-4}$, $C_{1-3}$, $C_{1-2}$, $C_{2-6}$, $C_{2-5}$, $C_{2-4}$, $C_{2-3}$, $C_{3-6}$, $C_{3-5}$, $C_{3-4}$ $C_{4-6}$, $C_{4-5}$, and $C_{5-6}$ alkyl.

As used herein, "alkyl" refers to a straight-chain or branched saturated hydrocarbon group having from 1 to 50 carbon atoms ("$C_{1-50}$ alkyl"). In some embodiments, an alkyl group has 1 to 40 carbon atoms ("$C_{1-40}$ alkyl"). In some embodiments, an alkyl group has 1 to 30 carbon atoms ("$C_{1-30}$ alkyl"). In some embodiments, an alkyl group has 1 to 20 carbon atoms ("$C_{1-20}$ alkyl"). In some embodiments, an alkyl group has 1 to 10 carbon atoms ("$C_{1-10}$ alkyl"). In some embodiments, an alkyl group has 1 to 9 carbon atoms ("$C_{1-9}$ alkyl"). In some embodiments, an alkyl group has 1 to 8 carbon atoms ("$C_{1-8}$ alkyl"). In some embodiments, an alkyl group has 1 to 7 carbon atoms ("$C_{1-7}$ alkyl"). In some embodiments, an alkyl group has 1 to 6 carbon atoms ("$C_{1-6}$ alkyl"). In some embodiments, an alkyl group has 1 to 5 carbon atoms ("$C_{1-5}$ alkyl"). In some embodiments, an alkyl group has 1 to 4 carbon atoms ("$C_{1-4}$ alkyl"). In some embodiments, an alkyl group has 1 to 3 carbon atoms ("$C_{1-3}$ alkyl"). In some embodiments, an alkyl group has 1 to 2 carbon atoms ("$C_{1-2}$ alkyl"). In some embodiments, an alkyl group has 1 carbon atom ("$C_1$ alkyl"). In some embodiments, an alkyl group has 2 to 6 carbon atoms ("$C_{2-6}$ alkyl"). Examples of $C_{1-6}$ alkyl groups include methyl ($C_1$), ethyl ($C_2$), n-propyl ($C_3$), isopropyl ($C_3$), n-butyl ($C_4$), tert-butyl ($C_4$), sec-butyl ($C_4$), iso-butyl ($C_4$), n-pentyl ($C_5$), 3-pentanyl ($C_5$), amyl ($C_5$), neopentyl ($C_5$), 3-methyl-2-butanyl ($C_5$), tertiary amyl ($C_5$), and n-hexyl ($C_6$). Additional examples of alkyl groups include n-heptyl ($C_7$), n-octyl ($C_8$) and the like. Unless otherwise specified, each instance of an alkyl group is independently unsubstituted (an "unsubstituted alkyl") or substituted (a "substituted alkyl") with one or more substituents. In certain embodiments, the alkyl group is an unsubstituted $C_{1-50}$ alkyl (e.g., —$CH_3$). In certain embodiments, the alkyl group is a substituted $C_{1-50}$ alkyl.

As understood from the above, alkyl groups, as defined herein, are, in certain embodiments, optionally substituted. Optionally substituted refers to a group which may be substituted or unsubstituted (e.g., "substituted" or "unsubstituted" alkyl, "substituted" or "unsubstituted" alkenyl, "substituted" or "unsubstituted" alkynyl, "substituted" or "unsubstituted" heteroalkyl, "substituted" or "unsubstituted" heteroalkenyl, "substituted" or "unsubstituted" heteroalkynyl, "substituted" or "unsubstituted" carbocyclyl, "substituted" or "unsubstituted" heterocyclyl, "substituted" or "unsubstituted" aryl or "substituted" or "unsubstituted" heteroaryl group). In general, the term "substituted" means that at least one hydrogen present on a group is replaced with a permissible substituent, e.g., a substituent which upon substitution results in a stable compound, e.g., a compound which does not spontaneously undergo transformation such as by rearrangement, cyclization, elimination, or other reaction. Unless otherwise indicated, a "substituted" group has a substituent at one or more substitutable positions of the group, and when more than one position in any given structure is substituted, the substituent is either the same or different at each position. For purposes of this invention, heteroatoms such as nitrogen may have hydrogen substituents and/or any suitable substituent as described herein which satisfy the valencies of the heteroatoms and results in the formation of a stable moiety.

Exemplary carbon atom substituents include, but are not limited to, halogen, —CN, —$NO_2$, —$N_3$, —$SO_2H$, —$SO_3H$, —OH, —$OR^{aa}$, —$ON(R^{bb})_2$, —$N(R^{bb})_2$, —$N(R^{bb})_3^+X^-$, —$N(OR^{cc})R^{bb}$, —SH, —$SR^{aa}$, —$SSR^{cc}$, —C(=O)$R^{aa}$, —$CO_2H$, —CHO, —C(O$R^{cc}$)$_2$, —$CO_2R^{aa}$, —OC(=O)$R^{aa}$, —$OCO_2R^{aa}$, —C(=O)N($R^{bb}$)$_2$, —OC(=O)N($R^{bb}$)$_2$, —$NR^{bb}$C(=O)$R^{aa}$, —$NR^{bb}CO_2R^{aa}$, —$NR^{bb}$C(=O)N($R^{bb}$)$_2$, —C(=$NR^{bb}$)$R^{aa}$, —C(=$NR^{bb}$)$OR^{aa}$, —OC(=$NR^{bb}$)$R^{aa}$, —OC(=$NR^{bb}$)$OR^{aa}$, —C(=$NR^{bb}$)N($R^{bb}$)$_2$, —OC(=$NR^{bb}$)N($R^{bb}$)$_2$, —$NR^{bb}$C(=$NR^{bb}$)N($R^{bb}$)$_2$, —C(=O)$NR^{bb}SO_2R^{aa}$, —$NR^{bb}SO_2R^{aa}$, —$SO_2N(R^{bb})_2$, —$SO_2R^{aa}$, —$SO_2OR^{aa}$, —$OSO_2R^{aa}$, —S(=O)$R^{aa}$, —OS(=O)$R^{aa}$, —Si($R^{aa}$)$_3$, —OSi($R^{aa}$)$_3$—C(=S)N($R^{bb}$)$_2$, —C(=O)$SR^{aa}$, —C(=S)$SR^{aa}$, —SC(=S)$SR^{aa}$, —SC(=O)$SR^{aa}$, —OC(=O)$SR^{aa}$, —SC(=O)O$R^{aa}$, —SC(=O)$R^{aa}$, —P(=O)$_2R^{aa}$, —OP(=O)$_2R^{aa}$, —P(=O)($R^{aa}$)$_2$, —OP(=O)($R^{aa}$)$_2$, —OP(=O)(O$R^{cc}$)$_2$, —P(=O)$_2$N($R^{bb}$)$_2$, —OP(=O)$_2$N($R^{bb}$)$_2$, —P(=O)(N$R^{bb}$)$_2$, —OP(=O)(N$R^{bb}$)$_2$, —$NR^{bb}$P(=O)(O$R^{cc}$)$_2$, —$NR^{bb}$P(=O)(N$R^{bb}$)$_2$, —P($R^{cc}$)$_2$, —P($R^{cc}$)$_3$, —OP($R^{cc}$)$_2$, —OP($R^{cc}$)$_3$, —B($R^{aa}$)$_2$, —B(O$R^{cc}$)$_2$, —B$R^{aa}$(O$R^{cc}$), $C_{1-10}$alkyl, $C_{1-10}$ perhaloalkyl, $C_{2-10}$ alkenyl, $C_{2-10}$ alkynyl, hetero$C_{1-10}$ alkyl, hetero$C_{2-10}$ alkenyl, hetero$C_{2-10}$ alkynyl, $C_{3-10}$ carbocyclyl, 3-14 membered heterocyclyl, $C_{6-14}$ aryl, and 5-14 membered heteroaryl, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 $R^{dd}$ groups;

or two geminal hydrogens on a carbon atom are replaced with the group =O, =S, =NN($R^{bb}$)$_2$, =NN$R^{bb}$C(=O) $R^{aa}$, =NN$R^{bb}$C(=O)O$R^{aa}$, =NN$R^{bb}$S(=O)$_2R^{aa}$, =N$R^{bb}$, or =NO$R^{cc}$;

each instance of $R^{aa}$ is, independently, selected from $C_{1-10}$ alkyl, $C_{1-10}$ perhaloalkyl, $C_{2-10}$ alkenyl, $C_{2-10}$ alkynyl, hetero$C_{1-10}$ alkyl, hetero$C_{2-10}$alkenyl, hetero$C_{2-10}$alkynyl, $C_{3-10}$ carbocyclyl, 3-14 membered heterocyclyl, $C_{6-14}$ aryl, and 5-14 membered heteroaryl, or two $R^{aa}$ groups are joined to form a 3-14 membered heterocyclyl or 5-14 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 $R^{dd}$ groups;

each instance of $R^{bb}$ is, independently, selected from hydrogen, —OH, —$OR^{aa}$, —$N(R^{cc})_2$, —CN, —C(=O)$R^{aa}$, —C(=O)N($R^{cc}$)$_2$, —$CO_2R^{aa}$, —$SO_2R^{aa}$, —C(=$NR^{cc}$)$OR^{aa}$, —C(=$NR^{cc}$)N($R^{cc}$)$_2$, —$SO_2N(R^{cc})_2$, —$SO_2R^{cc}$, —$SO_2R^{cc}$, —$SOR^{aa}$, —C(=S)N($R^{cc}$)$_2$, —C(=O)$SR^{cc}$, —C(=S)$SR^{cc}$, —P(=O)$_2R^{aa}$, —P(=O)($R^{aa}$)$_2$, —P(=O)$_2$N($R^{cc}$)$_2$, —P(=O)($NR^{cc}$)$_2$, $C_{1-10}$ alkyl, $C_{1-10}$ perhaloalkyl, $C_{2-10}$ alkenyl, $C_{2-10}$ alkynyl, hetero$C_{1-10}$alkyl, hetero$C_{2-10}$ alkenyl, hetero$C_{2-10}$alkynyl, $C_{3-10}$ carbocyclyl, 3-14 membered heterocyclyl, $C_{6-14}$ aryl, and 5-14 membered heteroaryl, or two $R^{bb}$ groups are joined to form a 3-14 membered heterocyclyl or 5-14 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 $R^{dd}$ groups;

each instance of $R^{cc}$ is, independently, selected from hydrogen, $C_{1-10}$ alkyl, $C_{1-10}$ perhaloalkyl, $C_{2-10}$ alkenyl, $C_{2-10}$ alkynyl, hetero$C_{1-10}$ alkyl, hetero$C_{2-10}$ alkenyl, hetero$C_{2-10}$ alkynyl, $C_{3-10}$ carbocyclyl, 3-14 membered heterocyclyl, $C_{6-14}$ aryl, and 5-14 membered heteroaryl, or two $R^{cc}$ groups are joined to form a 3-14 membered heterocyclyl or 5-14 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 $R^{dd}$ groups;

each instance of $R^{dd}$ is, independently, selected from halogen, —CN, —$NO_2$, —$N_3$, —$SO_2H$, —$SO_3H$, —OH, —$OR^{ee}$, —ON($R^{ff}$)$_2$, —N($R^{ff}$)$_2$, —N($R^{ff}$)$_3^+X^-$, —N($OR^{ee}$)$R^{ff}$, —SH, —$SR^{ee}$, —$SSR^{ee}$, —C(=O)$R^{ee}$, —$CO_2H$, —$CO_2R^{ee}$, —OC(=O)$R^{ee}$, —$OCO_2R^{ee}$, —C(=O)N($R^{ff}$)$_2$, —OC(=O)N($R^{ff}$)$_2$, —$NR^{ff}$C(=O)$R^{ee}$, —$NR^{ff}CO_2R^{ee}$, —$NR^{ff}$C(=O)N($R^{ff}$)$_2$, —C(=$NR^{ff}$)$OR^{ee}$, —OC(=$NR^{ff}$)$R^{ee}$, —OC(=$NR^{ff}$)$OR^{ee}$, —C(=$NR^{ff}$)N($R^{ff}$)$_2$, —OC(=$NR^{ff}$)N($R^{ff}$)$_2$, —$NR^{ff}$C(=$NR^{ff}$)N($R^{ff}$)$_2$, —$NR^{ff}SO_2R^{ee}$, —$SO_2N(R^{ff})_2$, —$SO_2R^{ee}$, —$SO_2OR^{ee}$, —$OSO_2R^{ee}$, —S(=O)$R^{ee}$, —Si($R^{ee}$)$_3$, —OSi($R^{ee}$)$_3$, —C(=S)N($R^{ff}$)$_2$, —C(=O)$SR^{ee}$, —C(=S)$SR^{ee}$, —SC(=S)$SR^{ee}$, —P(=O)$_2R^{ee}$, —P(=O)($R^{ee}$)$_2$, —OP(=O)($R^{ee}$)$_2$, —OP(=O)($OR^{ee}$)$_2$, $C_{1-6}$ alkyl, $C_{1-6}$ perhaloalkyl, $C_{2-6}$ alkenyl, $C_{2-6}$ alkynyl, hetero$C_{1-6}$alkyl, hetero$C_{2-6}$alkenyl, hetero$C_{2-6}$alkynyl, $C_{3-10}$ carbocyclyl, $C_{6-10}$ aryl, 5-10 membered heteroaryl, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 $R^{gg}$ groups, or two geminal $R^{dd}$ substituents can be joined to form =O or =S;

each instance of $R^{ee}$ is, independently, selected from $C_{1-6}$ alkyl, $C_{1-6}$ perhaloalkyl, $C_{2-6}$ alkenyl, $C_{2-6}$ alkynyl, hetero$C_{1-6}$ alkyl, hetero$C_{2-6}$alkenyl, hetero$C_{2-6}$ alkynyl, $C_{3-10}$ carbocyclyl, $C_{6-10}$ aryl, 3-10 membered heterocyclyl, and 3-10 membered heteroaryl, wherein each alkyl, alkenyl, alkynyl, heteroalkyl, heteroalkenyl, heteroalkynyl, carbocyclyl, heterocyclyl, aryl, and heteroaryl is independently substituted with 0, 1,2, 3, 4, or 5 $R^{gg}$ groups;

each instance of $R^{ff}$ is, independently, selected from hydrogen, $C_{1-6}$ alkyl, $C_{1-6}$ perhaloalkyl, $C_{2-6}$ alkenyl, $C_{2-6}$ alkynyl, hetero$C_{1-6}$alkyl, hetero$C_{2-6}$alkenyl, hetero$C_{2-6}$alkynyl, $C_{3-10}$ carbocyclyl, 3-10 membered heterocyclyl, $C_{6-10}$ aryl and 5-10 membered heteroaryl, or two $R^{ff}$ groups are joined to form a 3-14 membered heterocyclyl or 5-14 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 $R^{gg}$ groups; and each instance of $R^{gg}$ is, independently, halogen, —CN, —$NO_2$, —$N_3$, —$SO_2H$, —$SO_3H$, —OH, —$OC_{1-6}$ alkyl, —ON($C_{1-6}$ alkyl)$_2$, —N($C_{1-6}$ alkyl)$_2$, —N($C_{1-6}$ alkyl)$_3^+X^-$, —NH($C_{1-6}$ alkyl)$_2^+X^-$, —$NH_2$($C_{1-6}$ alkyl)$^+X^-$, —$NH_3^+X^-$, —N($OC_{1-6}$ alkyl)($C_{1-6}$ alkyl), —N(OH)($C_{1-6}$ alkyl), —NH(OH), —SH, —$SC_{1-6}$ alkyl, —SS($C_{1-6}$ alkyl), —C(=O)($C_{1-6}$ alkyl), —$CO_2H$, —$CO_2$($C_{1-6}$ alkyl), —OC(=O)($C_{1-6}$ alkyl), —$OCO_2$($C_{1-6}$ alkyl), —C(=O)$NH_2$, —C(=O)N($C_{1-6}$ alkyl)$_2$, —OC(=O)NH($C_{1-6}$ alkyl), —NHC(=O)($C_{1-6}$ alkyl), —N($C_{1-6}$ alkyl)C(=O)($C_{1-6}$ alkyl), —$NHCO_2$($C_{1-6}$ alkyl), —NHC(=O)N($C_{1-6}$ alkyl)$_2$, —NHC(=O)NH($C_{1-6}$ alkyl), —NHC(=O)$NH_2$, —C(=NH)O($C_{1-6}$ alkyl), —OC(=NH)($C_{1-6}$ alkyl), —OC(=NH)$OC_{1-6}$ alkyl, —C(=NH)N($C_{1-6}$ alkyl)$_2$, —C(=NH)NH($C_{1-6}$ alkyl), —C(=NH)$NH_2$, —OC(=NH)N($C_{1-6}$ alkyl)$_2$, —OC(NH)NH($C_{1-6}$ alkyl), —OC(NH)$NH_2$, —NHC(NH)N($C_{1-6}$ alkyl)$_2$, —NHC(=NH)$NH_2$, —$NHSO_2$($C_{1-6}$ alkyl), —$SO_2N$($C_{1-6}$ alkyl)$_2$, —$SO_2NH$($C_{1-6}$ alkyl), —$SO_2NH_2$, —$SO_2C_{1-6}$ alkyl, —$SO_2OC_{1-6}$ alkyl, —$OSO_2C_{1-6}$ alkyl, —$SOC_{1-6}$ alkyl, —Si($C_{1-6}$ alkyl)$_3$, —OSi($C_{1-6}$ alkyl)$_3$-C(=S)N($C_{1-6}$ alkyl)$_2$, C(=S)NH($C_{1-6}$alkyl), C(=S)$NH_2$, —C(=O)S($C_{1-6}$ alkyl), —C(=S)$SC_{1-6}$ alkyl, —SC(=S)$SC_{1-6}$ alkyl, —P(=O)$_2$($C_{1-6}$ alkyl), —P(=O)($C_{1-6}$ alkyl)$_2$, —OP(=O)($C_{1-6}$ alkyl)$_2$, —OP(O)($OC_{1-6}$ alkyl)$_2$, $C_{1-6}$ alkyl, $C_{1-6}$ perhaloalkyl, $C_{2-6}$ alkenyl, $C_{2-6}$ alkynyl, hetero$C_{1-6}$alkyl, hetero$C_{2-6}$alkenyl, hetero$C_{2-6}$alkynyl, $C_{3-10}$ carbocyclyl, $C_{6-10}$ aryl, 3-10 membered heterocyclyl, 5-10 membered heteroaryl; or two geminal $R^{gg}$ substituents can be joined to form =O or =S; wherein $X^-$ is a counterion.

In certain embodiments, a carbon atom substituent is selected from the group consisting of halogen, —CN, —$NO_2$, —$N_3$, —$SO_2H$, —$SO_3H$, —OH, —$OR^{aa}$, —N($R^{bb}$)$_2$, —SH, —$SR^{aa}$, —C(=O)$R^{aa}$, —$CO_2H$, —CHO, —$CO_2R^{aa}$, —OC(=O)$R^{aa}$, —$OCO_2R^{aa}$, —C(=O)N($R^{bb}$)$_2$, —OC(=O)N($R^{bb}$)$_2$, —$NR^{bb}$C(=O)$R^{aa}$, —$NR^{bb}CO_2R^{aa}$, —$NR^{bb}$C(=O)N($R^{bb}$)$_2$, —C(=O)$NR^{bb}SO_2R^{aa}$, —$NR^{bb}SO_2R^{aa}$, —$SO_2N(R^{bb})_2$, —$SO_2R^{aa}$, —S(=O)$R^{aa}$, —Si($R^{aa}$)$_3$, $C_{1-10}$ alkyl, $C_{1-10}$ perhaloalkyl, $C_{2-10}$ alkenyl, $C_{2-10}$ alkynyl, hetero$C_{1-10}$ alkyl, hetero$C_{2-10}$ alkenyl, hetero$C_{2-10}$ alkynyl, $C_{3-10}$ carbocyclyl, 3-14 membered heterocyclyl, $C_{6-14}$ aryl, and 5-14 membered heteroaryl, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 $R^{dd}$ groups.

EXAMPLES

The following examples are intended to illustrate certain embodiments of the present invention, but do not exemplify the full scope of the invention.

Example 1

This example describes formation of adhesive films containing various polyacrylic acids using a two-step non-aqueous dispersion and displacement method, and the determination of the burst strength of the resulting adhesive films. The adhesive films formed using the two-step non-aqueous dispersion and displacement method had relatively high burst strengths.

Adhesive films were made from 13 different polyacrylic acids. The product number and molecular weight of each of the polyacrylic acids can be found in Table 1. The polyacrylic acids differed in viscosity average molecular weight. The Carbopol products were cross-linked.

TABLE 1

Various Polyacrylic acids

| Product | Molecular Weight |
|---|---|
| Sigma 181285 | 450,000 |
| Sigma 306215 | 1,250,000 |
| Sigma 306223 | 3,000,000 |
| Sigma | 3,000,000 |
| Carbopol 971P NF | >1,000,000,000 |
| Carbopol 980 | >1,000,000,000 |
| Carbopol 981 NF | >1,000,000,000 |
| Carbopol 5984 EP | >1,000,000,000 |
| Carbopol 71G NF | >1,000,000,000 |
| Carbopol PEMULEN 9TM TR-1 | >1,000,000,000 |
| Carbopol PEMULEN ™ TR-2 | >1,000,000,000 |
| Carbopol Noveon AA-1 | >1,000,000,000 |
| Carbopol 974 | >1,000,000,000 |

All films were made using a two-step non-aqueous dispersion and displacement method. Ethyl acetate was used as a dispersant and ethanol was used as the displacement solvent. Briefly, films were made by adding 1.66 grams of the polyacrylic acid powder to 12 mL of ethyl acetate. The polyacrylic acid/ethyl acetate mixture was then spread out as a 4 inch×4 inch sheet, and after 12 minutes the dispersed film was exposed to a mist spray of 200 proof ethanol. The film was then dried for 72 hours and evaluated for burst pressure testing as described above. All films contained 99% of a single polyacrylic acid, except the Nov/Carb film which contained a 50/50 (w/w) mixture of Noveon and Carbopol 974.

Figure 3:
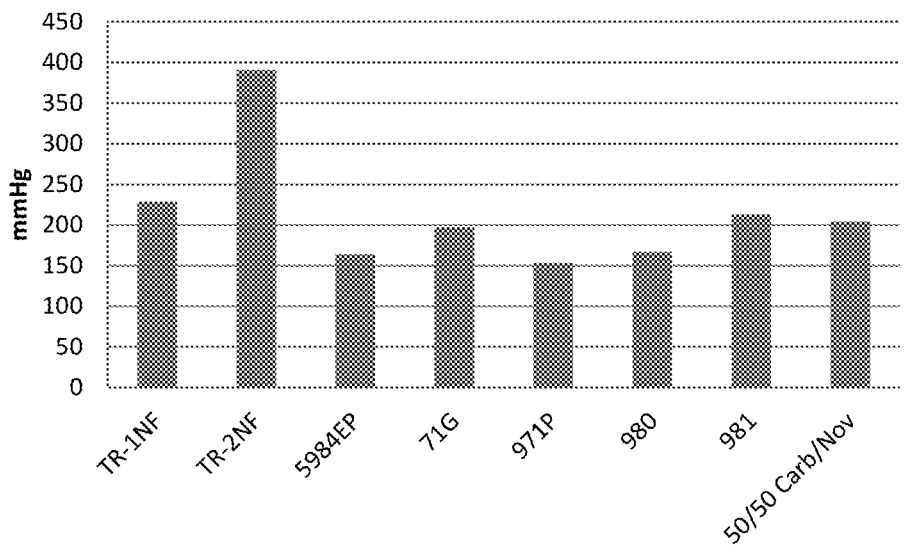
FIG. 3 is, according to certain embodiments, graphs of burst pressure for adhesive compositions comprising various polyacrylic acids.
Figure 3:
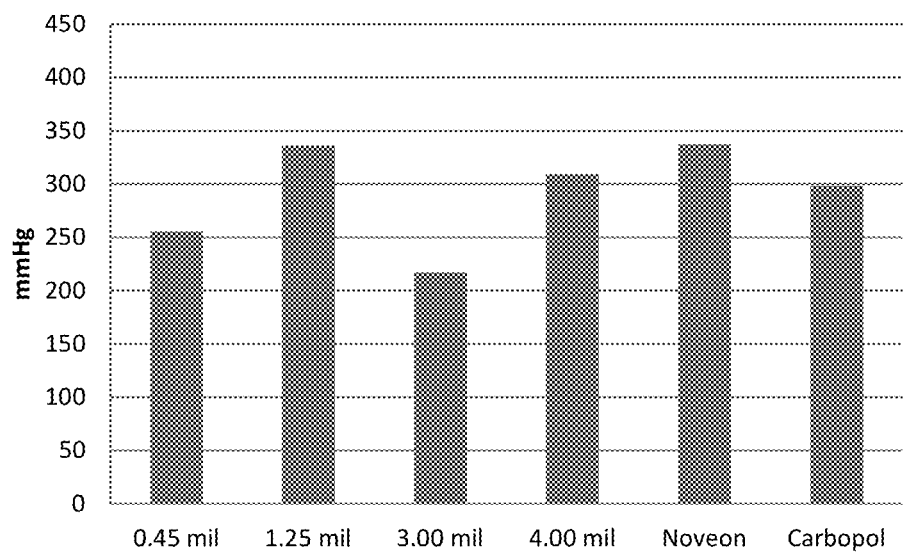

FIG. 3 shows the burst pressure for the adhesive films made with various polyacrylic acids. All polyacrylic acid polymer films had a burst pressure greater than 150 mmHg gauge.

Comparative Example 1

This example provides a comparison between adhesive films made using different methods of formation. Adhesive films were made using the two-step non-aqueous dispersion and displacement method described in Example 1 and via a one-step method, which utilized water. The films formed via the method utilizing water had a lower burst pressure compared to the films formed using the two-step non-aqueous dispersion and displacement method described in Example 1.

The films formed via the method utilizing water were formed from 50/50 (w/w) mixture of Noveon and Carbopol 974, TR-1NF, Sigma MW 1,250,000, and 71G-NF by adding 0.2 grams of each polymer powder to 1.5 mL of water individually. The powder and water mixture was applied over a 3.0 mm biopsy punch hole as described in ASTM F2392-04. After 5 minutes of incubation the burst pressure test was initiated and burst pressure was recorded in mmHg.

The films made using the two-step non-aqueous dispersion and displacement method described in Example 1, were made by adding 1.66 grams of 50/50 (w/w) mixture of Noveon and Carbopol 974 to 12 mL of ethyl acetate, the polyacrylic acid/ethyl acetate mixture was then spread out as a 4 inch×4 inch sheet, and after 12 minutes the dispersed film was exposed to a mist spray of 200 proof ethanol. The film was then dried for 72 hours prior to testing.

Figure 4A:
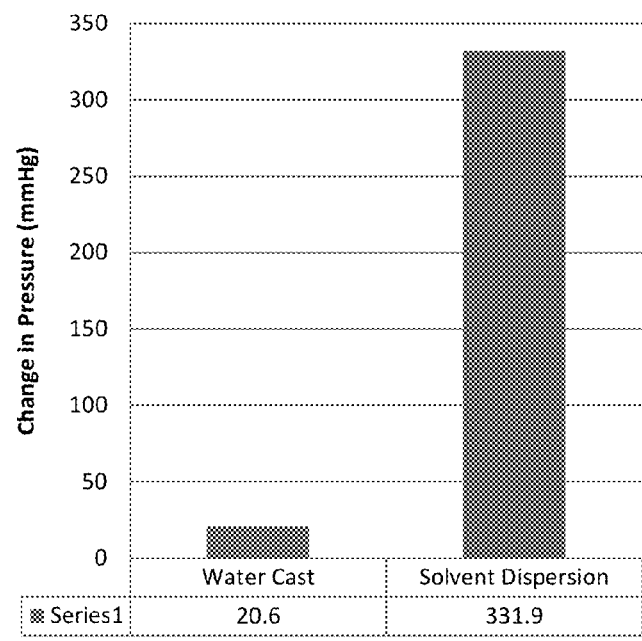
FIG. 4A is a graph of burst pressure for adhesive compositions manufactured using various methods, according to some embodiments.
Figure 4B:
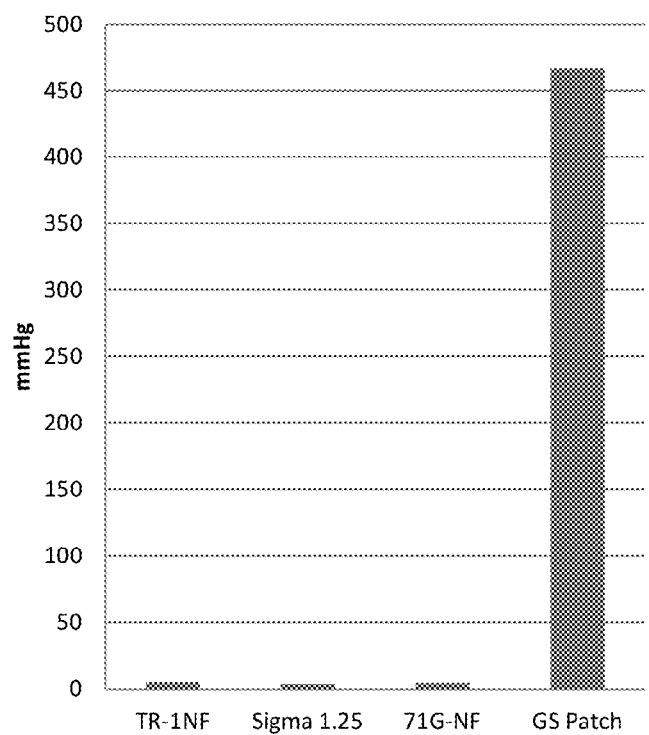
FIG. 4B is a graph of burst pressure for adhesive compositions manufactured using various methods, according to some embodiments.

FIG. 4A shows the burst pressure for the adhesive films made from 50/50 (w/w) mixture of Noveon and Carbopol 974 via the method involving water (referred to as "water cast") and the two-step non-aqueous method (referred to as "solvent dispersion"). FIG. 4B shows the burst pressure for the adhesive films made from various polyacrylic acids via the method involving water (referred to as "water cast") and the two-step non-aqueous method (referred to as "solvent dispersion"). Films formed via aqueous methods had a significantly lower burst pressure (i.e., less than 50 mmHg (gauge)) than films formed from the methods, described herein.

Comparative Example 2

This example compares the lap shear strength of adhesive compositions formed from powder alone, a single organic solvent method, and the two-step non-aqueous dispersion and displacement method described in Example 1. The films formed as described in Example 1 had the highest lap shear strength.

Three different polyacrylic acid (PAA) films were formed to evaluate the influence of the formation method on lap shear strength. The different compositions were: i) a blend of 50% Carbopol 974P NF and 50% Noveon AA-1; ii) Carbopol 971P NF; and Polyacrylic acid average MW 1,250,000.

According to the powder method, 0.2 g of each powder was evenly distributed onto the bottom of a 2×2.5 cm section of a glass microscope slide (Gold Seal, Portsmouth, N.H., Cat#: 3049). A spray bottle with water was then used to spray a second glass microscope slide and the two microscope slides were adhered together over the 2×2.5 cm overlap using moderate pressure. The two microscope slides were then incubated at 37° C. for 5 minutes.

The single non-aqueous polar solvent method was an ethanol solvent casting method. Briefly, 0.2 g of each PAA adhesive powder was mixed with 0.35 mL of 200 proof ethanol to form a heavy paste. The PAA/ethanol paste was then spread evenly over the bottom 2×2.5 cm section of a glass microscope slide (Gold Seal, Portsmouth, N.H., Cat#: 3049). The slide was then allowed to dry for 24 hours at room temperature. After drying, a spray bottle with water was used to spray a second glass microscope slide and the two microscope slides were adhered together over the 2×2.5 cm overlap using moderate pressure. The two microscope slides were then incubated at 37° C. for 5 minutes.

The two-step non-aqueous dispersion and displacement method described in Example 1 included mixing 0.1 g of each PAA adhesive powder with 0.75 mL of ethyl acetate (Sigma Aldrich, Cat#270989) to make a mixture. The PAA/ethyl acetate mixture was then poured evenly over the bottom 2×2.5 cm section of a glass microscope slide (Gold Seal, Portsmouth, N.H., Cat#: 3049). The slide was then allowed to dry for 12 minutes at room temperature after which the coated slide was sprayed with a mixture of 99% ethanol and 1% glycerin and then allowed to dry at room temperature for 24 hours. After drying, a spray bottle with water was used to spray a second glass microscope slide and the two microscope slides were adhered together over the 2×2.5 cm overlap using moderate pressure. The two microscope slides were then incubated at 37° C. for 5 minutes.

Adhesive strength via lap shear testing was analyzed using a Test Resources Model 100Q225-6 Universal Test Machine with a 10 lb load cell as described above. In short, the two adhered microscope slides were locked into position on the test machine using manual screw type grips. The two microscope slides were then pulled apart at a rate of 150 mm/min and data was recorded using the accompanying XY software.

Figure 5:
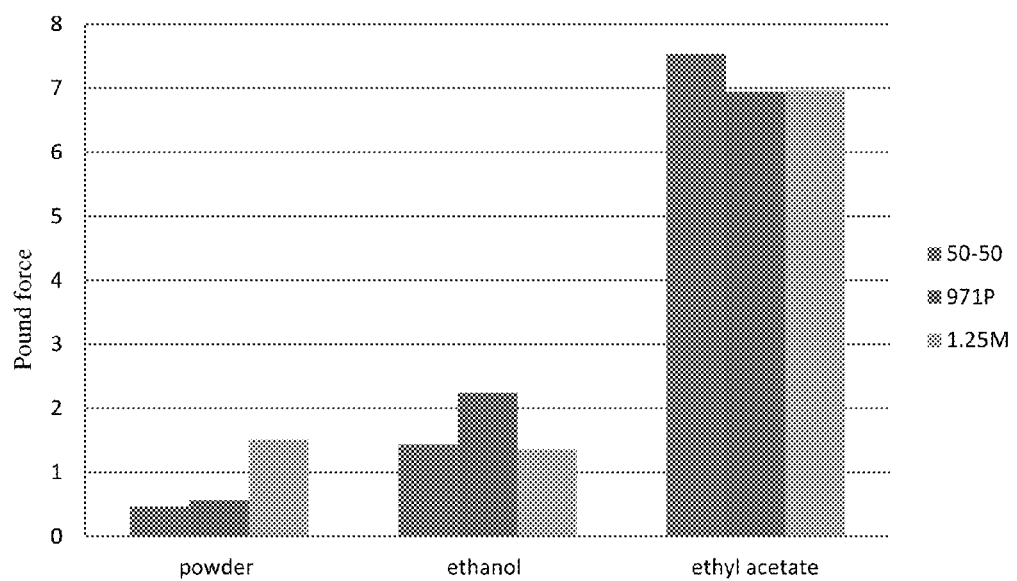
FIG. 5 is a graph of maximum load for adhesive compositions manufactured using various methods, according to one set of embodiments.

FIG. 5 shows the lap shear data for the adhesive films. Films formed via the powder and ethanol casting methods had a significantly lower lap shear strength than films formed using the two-step non-aqueous dispersion and displacement method.

Example 2

This example describes the effect of total polyacrylic acid weight percentage on the adhesive and mechanical properties of an adhesive matrix. Adhesive matrices containing 25 wt. % filler and 75 wt. % of a 50:50 (w/w) Carbopol 974P NF and Noveon AA-1 blend had a lower burst strength than films containing about 99 wt. % of the 50:50 (w/w) Carbopol 974P NF and Noveon AA-1 blend.

All films were formed by the two-step non-aqueous dispersion and displacement method described in Comparative Example 2, except different components were used to make the films.

The films including filler contained 75 wt. % of a blend of a 50:50, by weight, blend of Carbopol 974P NF and Noveon AA-1, mixed with 25 wt. % binder. Various binders that were tested included Karaya gum (1), Gelatin from porcine skin (2), Carboxymethylcellulose (3), Gum Arabic (4), Sodium Alginate (5), or Polyvinylpyrrolidone (6).

The films without fillers contained 99 wt. % of the 50:50, by weight, blend of Carbopol 974P NF and Noveon AA-1 (7).

Figure 6:
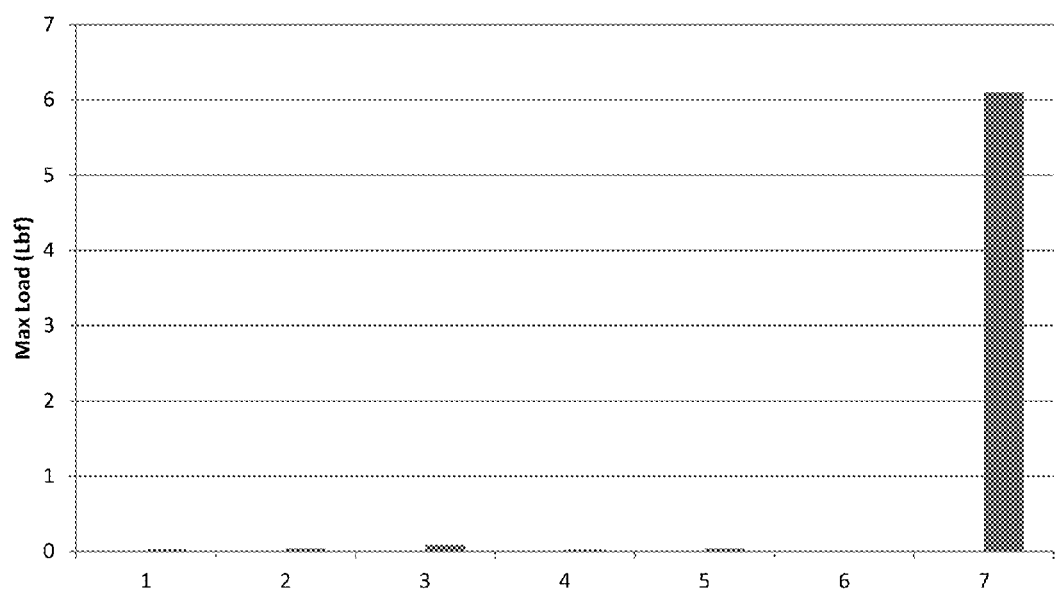
FIG. 6 is a graph of maximum load for adhesive compositions with various weight percentages of polyacrylic acid, according to one set of embodiments.

FIG. 6 shows the lap shear data for the adhesive films. Films formed with filler had a significantly lower lap shear strength than films formed from the two-step non-aqueous dispersion and displacement method.

Example 3

This example describes the formation of an adhesive matrix containing polyacrylic acid using a single-step spraying process, and the determination of the burst strength of the resulting adhesive matrix. The adhesive matrix that was formed using the single-step spraying process had a relatively high burst strength.

A 15 wt. % polyacrylic acid solution was formed from equal amounts of the polyacrylic acids Carbopol 974P NF and Noveon AA-1 dissolved in Specially Denatured Alcohol (which is composed of 95% ethanol and 5% isopropanol). This solution was mixed for several minutes and then sprayed at 35 cc/min onto a small intestine submucosa (SIS) patch using a pressure-based Gapptec system. The pressure-based Gapptec system included a Cobra 3C Precision Applicator, a TS1 Air Cap, a 1.0 mm fluid tip, a Binks SG2 pressure pot (containing a fluid reservoir and no pressure), a DDP with Beinlich ECO pump operated at 1.2 cc/rev and siphoned, and 1/16" ID FEP fluoropolymer tubing. The patch was coated 5 times and then allowed to dry overnight at 115° F.

The coated SIS patch was cut into three 1 cm² squares, and the adhesive burst strengths of the squares were assessed. Each square was moistened with about 200 µL of water and adhered to a sausage casing over a 4 mm biopsy punch hole. The patches and the adhesive substrates were then incubated for 5 minutes at 37° C., cut to the appropriate size, and clamped to a test fixture as described in ASTM F 2392-04. Then, water was gradually pumped into the fixture using a syringe pump while the pressure was recorded using an ESI Technology USB pressure transducer. The pressure was increased until the patch squares detached from the adhesive substrate due to adhesion failure, at which point the maximum adhesive burst pressure was recorded. Table 2 (below) summarizes the results.

TABLE 2

Measured burst pressures for adhesive substrates formulated by coating polyacrylic acid using a one-step spraying process.

| Square # | Burst pressure (gauge, mmHg) | Failure Type |
| --- | --- | --- |
| 1 | 290 | adhesive |
| 2 | 415 | adhesive |
| 3 | 555 | adhesive |

While several embodiments of the present invention have been described and illustrated herein, those of ordinary skill in the art will readily envision a variety of other means and/or structures for performing the functions and/or obtaining the results and/or one or more of the advantages described herein, and each of such variations and/or modifications is deemed to be within the scope of the present invention. More generally, those skilled in the art will readily appreciate that all parameters, dimensions, materials, and configurations described herein are meant to be exemplary and that the actual parameters, dimensions, materials, and/or configurations will depend upon the specific application or applications for which the teachings of the present invention is/are used. Those skilled in the art will recognize, or be able to ascertain using no more than routine experimentation, many equivalents to the specific embodiments of the invention described herein. It is, therefore, to be understood that the foregoing embodiments are presented by way of example only and that, within the scope of the appended claims and equivalents thereto, the invention may be practiced otherwise than as specifically described and claimed. The present invention is directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the scope of the present invention.

In the claims, as well as in the specification above, all transitional phrases such as "comprising," "including," "carrying," "having," "containing," "involving," "holding," and the like are to be understood to be open-ended, i.e., to mean including but not limited to. Only the transitional phrases "consisting of" and "consisting essentially of" shall be closed or semi-closed transitional phrases, respectively.

What is claimed is:

1. A method of forming an adhesive matrix, comprising:
    establishing a mixture comprising at least one non-aqueous solvent and at least one polyacrylic acid on a substrate to form a deposit of the mixture on the substrate;
    wherein at least a portion of the at least one non-aqueous solvent is evaporated from the deposit to produce the adhesive matrix, and
    less than about 8 wt. % of the adhesive matrix is made up of liquid.

2. The method of claim 1, wherein the mixture contains the at least one non-aqueous solvent in an amount of from about 50 wt. % to about 99.9 wt. %.

3. The method of claim 1, wherein the mixture contains the at least one polyacrylic acid in an amount of from about 0.1 wt. % to about 25 wt. %.

4. A method of forming an adhesive matrix, comprising:
establishing a mixture comprising at least one non-aqueous solvent and at least one polyacrylic acid on a substrate to form a deposit of the mixture on the substrate, wherein:
the mixture contains the at least one non-aqueous solvent in an amount of from about 50 wt. % to about 99.9 wt. %;
the mixture contains the at least one polyacrylic acid in an amount of from about 0.1 wt. % to about 25 wt. %; and
at least a portion of the at least one non-aqueous solvent is evaporated from the deposit to produce the adhesive matrix.

5. The method of claim 1, wherein less than about 8 wt. % of the adhesive matrix is made up of residual solvent.

6. The method of claim 1, wherein, at at least one point in time within 90 days of forming the deposit on the substrate, less than about 8 wt. % of the adhesive matrix is made up of liquid.

7. The method of claim 1, wherein, at at least one point in time within 90 days of forming the deposit on the substrate, less than about 8 wt. % of the adhesive matrix is made up of residual solvent.

8. The method of claim 1, wherein the at least one non-aqueous solvent comprises at least one alcohol.

9. The method of claim 8, wherein the alcohol content of the solvent component of the mixture is at least about 50 wt. %.

10. The method of claim 8, wherein the at least one alcohol comprises at least one of methanol, ethanol, propanol, and butanol.

11. The method of claim 1, wherein the at least one polyacrylic acid comprises a polyacrylic acid crosslinked with pentaerythritol and/or allyl sucrose.

12. The method of claim 1, wherein the at least one polyacrylic acid comprises a polyacrylic acid crosslinked with divinyl glycol.

13. The method of claim 1, wherein the mixture contains less than or equal to about 0.1 wt. % water.

14. The method of claim 1, wherein the weight percentage of polyacrylic acid in the adhesive matrix is greater than or equal to about 90 wt. %.

15. The method of claim 1, wherein the substrate comprises small intestinal submucosa and/or fibrin.

16. The method of claim 1, wherein the adhesive matrix has a burst strength of at least about 100 mmHg gauge.

17. The method of claim 1, wherein the adhesive matrix has a lap shear adhesive strength of greater than or equal to about 1.0 pound force.

18. The method of claim 1, wherein the adhesive matrix has a thickness of less than about 1 mm.

19. The method of claim 1, wherein the mass of the adhesive matrix on the substrate is from about 2 $mg/cm^2$ to about 35 $g/cm^2$.

20. The method of claim 1, wherein the establishing the mixture comprises applying a pressure to the mixture and spraying the mixture through a nozzle.

21. The method of claim 1, wherein the adhesive matrix is a water-activated adhesive matrix.

22. The method of claim 4, wherein less than about 8 wt. % of the adhesive matrix is made up of residual solvent.

23. The method of claim 4, wherein, at at least one point in time within 90 days of forming the deposit on the substrate, less than about 8 wt. % of the adhesive matrix is made up of residual solvent.

24. The method of claim 4, wherein the at least one non-aqueous solvent comprises at least one alcohol.

25. The method of claim 24, wherein the alcohol content of the solvent component of the mixture is at least about 50 wt. %.

26. The method of claim 24, wherein the at least one alcohol comprises at least one of methanol, ethanol, propanol, and butanol.

27. The method of claim 4, wherein the at least one polyacrylic acid comprises a polyacrylic acid crosslinked with pentaerythritol and/or allyl sucrose.

28. The method of claim 4, wherein the at least one polyacrylic acid comprises a polyacrylic acid crosslinked with divinyl glycol.

29. The method of claim 4, wherein the mixture contains less than or equal to about 0.1 wt. % water.

30. The method of claim 4, wherein the adhesive matrix has a burst strength of at least about 100 mm Hg gauge.

31. The method of claim 4, wherein the adhesive matrix has a lap shear adhesive strength of greater than or equal to about 1.0 pound force.

32. The method of claim 4, wherein the adhesive matrix is a water-activated adhesive matrix.

* * * * *

UNITED STATES PATENT AND TRADEMARK OFFICE
CERTIFICATE OF CORRECTION

PATENT NO.         : 9,833,538 B2                               Page 1 of 1
APPLICATION NO.    : 14/983396
DATED              : December 5, 2017
INVENTOR(S)        : Daniel Grant Ericson et al.

It is certified that error appears in the above-identified patent and that said Letters Patent is hereby corrected as shown below:

In the Specification

At Column 7, Line 63, the words "equal to about 80%/o" should read --equal to about 80%--

At Column 16, Line 10, the words "equal to about mL/minute" should read --equal to about 20 mL/minute--

At Column 36, Line 17, the word "veridical" should read --virucidal--

At Column 36, Line 38, the word "locidem™" should read --locide™--

Signed and Sealed this
Thirtieth Day of January, 2018

Joseph Matal
*Performing the Functions and Duties of the*
*Under Secretary of Commerce for Intellectual Property and*
*Director of the United States Patent and Trademark Office*